US009035133B2

(12) United States Patent
Leon et al.

(10) Patent No.: US 9,035,133 B2
(45) Date of Patent: May 19, 2015

(54) HERBICIDE-RESISTANT SUNFLOWER PLANTS AND METHODS OF USE

(75) Inventors: Alberto Javier Leon, Mar del Plata (AR); Monica Mariel Morata, Mar del Plata (AR); Andres Daniel Zambelli, Mar del Plata (AR)

(73) Assignees: BASF AGROCHEMICAL PRODUCTS B.V., Arnhem (NL); ADVANTA SEEDS B.V., Kappelle (NL)

( * ) Notice: Subject to any disclaimer, the term of this patent is extended or adjusted under 35 U.S.C. 154(b) by 1742 days.

(21) Appl. No.: 12/517,919

(22) PCT Filed: Dec. 11, 2007

(86) PCT No.: PCT/EP2007/063737
§ 371 (c)(1),
(2), (4) Date: Oct. 11, 2011

(87) PCT Pub. No.: WO2008/071715
PCT Pub. Date: Jun. 19, 2008

(65) Prior Publication Data
US 2012/0023601 A1    Jan. 26, 2012

Related U.S. Application Data

(60) Provisional application No. 60/874,309, filed on Dec. 12, 2006.

(51) Int. Cl.
*A01H 5/10* (2006.01)
*C12N 15/82* (2006.01)
*A01H 1/00* (2006.01)

(52) U.S. Cl.
CPC .............. *C12N 15/8274* (2013.01); *A01H 1/00* (2013.01); *A01H 5/10* (2013.01)

(58) Field of Classification Search
None
See application file for complete search history.

(56) References Cited

U.S. PATENT DOCUMENTS

| | | | |
|---|---|---|---|
| 4,443,971 A | 4/1984 | Chaleff | |
| 4,761,373 A | 8/1988 | Anderson et al. | |
| 4,774,381 A | 9/1988 | Chaleff et al. | |
| 5,013,659 A | 5/1991 | Bedbrook et al. | |
| 5,084,082 A | 1/1992 | Sebastian | |
| 5,116,402 A | 5/1992 | Dutka et al. | |
| 5,141,870 A | 8/1992 | Bedbrook et al. | |
| 5,198,599 A | 3/1993 | Thill | |
| 5,304,732 A | 4/1994 | Anderson et al. | |
| 5,331,107 A | 7/1994 | Anderson et al. | |
| 5,378,824 A | 1/1995 | Bedbrook et al. | |
| 5,478,789 A | 12/1995 | Hattori et al. | |
| 5,478,798 A | 12/1995 | Mayer et al. | |
| 5,488,029 A | 1/1996 | Hamprecht et al. | |
| 5,539,092 A | 7/1996 | Haselkorn et al. | |
| 5,545,822 A | 8/1996 | Croughan | |
| 5,595,890 A | 1/1997 | Newton et al. | |
| 5,597,717 A | 1/1997 | Guerireau et al. | |
| 5,605,011 A | 2/1997 | Bedbrook et al. | |
| 5,633,437 A | 5/1997 | Bernasconi et al. | |
| 5,633,444 A | 5/1997 | Guerineau et al. | |
| 5,643,779 A | 7/1997 | Ehrlich et al. | |
| RE35,661 E | 11/1997 | Thill | |
| 5,718,079 A | 2/1998 | Anderson et al. | |
| 5,719,046 A | 2/1998 | Guerieneau et al. | |
| 5,731,180 A | 3/1998 | Dietrich | |
| 5,736,629 A | 4/1998 | Croughan | |
| 5,767,361 A | 6/1998 | Dietrich | |
| 5,767,366 A | 6/1998 | Sathaswan et al. | |
| 5,773,702 A | 6/1998 | Penner et al. | |
| 5,773,703 A | 6/1998 | Croughan | |
| 5,773,704 A | 6/1998 | Croughan | |
| 5,821,126 A | 10/1998 | Durzan | |
| 5,853,973 A | 12/1998 | Kakefuda et al. | |
| 5,858,652 A | 1/1999 | Laffler et al. | |
| 5,859,348 A | 1/1999 | Penner et al. | |
| 5,876,932 A | 3/1999 | Fischer | |
| 5,928,937 A | 7/1999 | Kakefuda et al. | |
| 5,952,553 A | 9/1999 | Croughan | |
| 6,043,196 A | 3/2000 | Mayer et al. | |
| 6,100,030 A | 8/2000 | McCasky Feazel et al. | |
| 6,114,116 A | 9/2000 | Lemieux et al. | |

(Continued)

FOREIGN PATENT DOCUMENTS

| | | |
|---|---|---|
| CA | 1335412 | 3/1988 |
| CA | 2340282 | 10/2001 |
| EP | 0154204 | 11/1985 |
| EP | 0257993 | 3/1988 |
| EP | 0360750 | 3/1990 |
| EP | 0364580 | 4/1990 |
| EP | 0375875 | 7/1990 |
| EP | 0461355 | 12/1991 |
| EP | 0502588 | 9/1992 |
| EP | 0508161 | 10/1992 |

(Continued)

OTHER PUBLICATIONS

Bruniard et al 2001, Helia 24(35): 11-16.*
Sala et al (2012, Proc. 18th Int. Sunflower Conf. Mar del Plata-Balcarce, Argentina, pp. 551-556.*
Al-Khatib, K., et al., Imazethapyr resistance in common sunflower (*Helianthus annuus*), *Weed Science*, 1998, vol. 46, pp. 403-407.
Inui, H., et al., "Herbicide resistance in transgenic plants with mammalian P450 monooxygenase genes," *Pest Management Science*, 2005, vol. 61, pp. 286-291.

(Continued)

*Primary Examiner* — David H Kruse
(74) *Attorney, Agent, or Firm* — Mintz, Levin, Cohn, Ferris, Glovsky And Popeo, P.C.

(57) ABSTRACT

Novel herbicide-resistant sunflower plants designated as MUT31 and herbicide-resistant descendents thereof are provided. The MUT31 sunflower plants and the herbicide-resistant descendents thereof comprise increased resistance to at least one imidazolinone herbicide, when compared to wild-type sunflower plants. Methods for controlling weeds in the vicinity of these herbicide-resistant sunflower plants and methods for increasing the herbicide-resistance of a sunflower plant are also provided.

13 Claims, 1 Drawing Sheet

(56) References Cited

U.S. PATENT DOCUMENTS

| | | | |
|---|---|---|---|
| 6,175,065 B1 | 1/2001 | Schmidt et al. |
| 6,207,425 B1 | 3/2001 | Liu et al. |
| 6,211,438 B1 | 4/2001 | Anderson et al. |
| 6,211,439 B1 | 4/2001 | Anderson et al. |
| 6,222,100 B1 | 4/2001 | Anderson et al. |
| 6,225,105 B1 | 5/2001 | Sathasivan et al. |
| 6,274,796 B1 | 8/2001 | Croughan |
| 6,339,184 B1 | 1/2002 | Smith |
| 6,348,643 B1 | 2/2002 | Kakefuda et al. |
| 6,358,686 B1 | 3/2002 | Lemieux et al. |
| 6,475,736 B1 | 11/2002 | Stanton, Jr. |
| 6,492,582 B2 | 12/2002 | Johnson |
| 6,613,963 B1 | 9/2003 | Gingera et al. |
| 6,627,401 B2 | 9/2003 | Ralhan |
| 6,696,294 B1 | 2/2004 | Konzak |
| 6,943,280 B2 | 9/2005 | Croughan |
| 7,019,196 B1 | 3/2006 | Croughan |
| 7,345,221 B2 | 3/2008 | Croughan |
| 7,399,905 B2 | 7/2008 | Croughan |
| 7,495,153 B2 | 2/2009 | Croughan |
| 7,595,177 B2 | 9/2009 | Barnes et al. |
| 7,754,947 B2 | 7/2010 | Croughan |
| 7,786,360 B2 | 8/2010 | Linscombe |
| 7,807,882 B2 | 10/2010 | Leon et al. |
| 2001/0044939 A1 | 11/2001 | Abell et al. |
| 2002/0120962 A1 | 8/2002 | Charne et al. |
| 2002/0138866 A1 | 9/2002 | Gingera et al. |
| 2002/0138881 A1 | 9/2002 | Charne et al. |
| 2003/0096277 A1 | 5/2003 | Chen |
| 2003/0097692 A1 | 5/2003 | Jander et al. |
| 2003/0138780 A1 | 7/2003 | Gill et al. |
| 2003/0180929 A1 | 9/2003 | Kafefuda et al. |
| 2003/0217381 A1 | 11/2003 | Croughan |
| 2004/0142353 A1 | 7/2004 | Cheung et al. |
| 2004/0171027 A1 | 9/2004 | Barnes et al. |
| 2004/0172729 A1 | 9/2004 | Moldenhauer et al. |
| 2004/0187178 A1 | 9/2004 | Slinkard et al. |
| 2004/0219675 A1 | 11/2004 | Sainz et al. |
| 2004/0237134 A1 | 11/2004 | Pozniak et al. |
| 2004/0244080 A1 | 12/2004 | Hucl |
| 2005/0044597 A1 | 2/2005 | Konzak |
| 2005/0198705 A1 | 9/2005 | Croughan |
| 2005/0208506 A1 | 9/2005 | Zhao et al. |
| 2005/0283858 A1 | 12/2005 | Yao et al. |
| 2006/0010514 A1 | 1/2006 | Birk et al. |
| 2006/0095992 A1 | 5/2006 | Bowran et al. |
| 2007/0028318 A1 | 2/2007 | Livore et al. |
| 2007/0033670 A1 | 2/2007 | Konzak et al. |
| 2007/0118920 A1 | 5/2007 | Leon et al. |
| 2008/0167186 A1 | 7/2008 | Croughan |
| 2008/0276329 A1 | 11/2008 | Moldenhauer |
| 2009/0025108 A1 | 1/2009 | Croughan |

FOREIGN PATENT DOCUMENTS

| | | |
|---|---|---|
| EP | 0525384 | 2/1993 |
| EP | 1754786 | 4/1996 |
| EP | 0730030 | 9/1996 |
| EP | 0965265 | 12/1999 |
| EP | 1033405 | 9/2000 |
| JP | 8214882 | 8/1996 |
| WO | WO9014000 | 11/1990 |
| WO | WO9113159 | 9/1991 |
| WO | WO9208794 | 5/1992 |
| WO | WO9633270 | 10/1996 |
| WO | WO9741218 | 11/1997 |
| WO | WO9802526 | 1/1998 |
| WO | WO9802527 | 1/1998 |
| WO | WO9832706 | 7/1998 |
| WO | WO 99/19493 A2 | 4/1999 |
| WO | WO9919493 | 4/1999 |
| WO | WO9953081 | 10/1999 |
| WO | WO9965292 | 12/1999 |
| WO | WO9965314 | 12/1999 |
| WO | WO0026390 | 5/2000 |
| WO | WO0027182 | 5/2000 |
| WO | WO0053763 | 9/2000 |
| WO | WO0121821 | 3/2001 |
| WO | WO 01/65922 A2 * | 9/2001 |
| WO | WO0165922 | 9/2001 |
| WO | WO0182685 | 11/2001 |
| WO | WO0183818 | 11/2001 |
| WO | WO0185970 | 11/2001 |
| WO | WO0192512 | 12/2001 |
| WO | WO0200915 | 1/2002 |
| WO | WO0208794 | 1/2002 |
| WO | WO02092820 | 11/2002 |
| WO | WO03012115 | 2/2003 |
| WO | WO03013225 | 2/2003 |
| WO | WO03014356 | 2/2003 |
| WO | WO03014357 | 2/2003 |
| WO | WO03076574 | 9/2003 |
| WO | WO2004007691 | 1/2004 |
| WO | WO2004016073 | 2/2004 |
| WO | WO2004022715 | 3/2004 |
| WO | WO2004040012 | 5/2004 |
| WO | WO2004106529 | 12/2004 |
| WO | WO2005020673 | 3/2005 |
| WO | WO2005093093 | 10/2005 |
| WO | WO2006007373 | 1/2006 |
| WO | WO 2006/024351 A1 | 3/2006 |
| WO | WO2006024351 | 3/2006 |
| WO | WO2006060634 | 6/2006 |
| WO | WO2006094084 | 9/2006 |
| WO | WO2007005581 | 1/2007 |
| WO | WO2007032807 | 3/2007 |
| WO | WO2007140451 | 12/2007 |
| WO | WO2008124495 | 10/2008 |
| WO | WO2009046334 | 4/2009 |

OTHER PUBLICATIONS

Kolkman, J., et al., "Acetohydroxyacid synthase mutations conferring resistance to imidazolinone or sulfonylurea herbicides in sunflower," *Theor Appl Genet*, 2004, vol. 109, pp. 1147-1159.

Pan, G., et al., "Map-based cloning of a novel rice cytochrome P450 gene *CYP81A6* that confers resistance to two different classes," *Plant Mol Biol*, 2006, vol. 61, pp. 933-943.

Tan, S., et al., "Imidazolinone-tolerant crops: history, current status and future," *Pest Management Science*, 2005, vol. 61, pp. 246-257.

Tan, S., et al., "Herbicidal inhibitors of amino acid biosynthesis and herbicide-tolerant crops," *Amino Acids*, 2006, vol. 30, pp. 195-204.

Werck-Reichhart, D., et al., "Cytochromes P450 for engineering herbicide tolerance," *trends in plant science Reviews*, 2000, vol. 5(3), pp. 116-123.

Yu, Q., et al., "Tolerance to acetolactate synthase and acetyl-coenzyme A carboxylase inhibiting herbicides in *Vulpia bromoides* is conferred by two co-existing resistance mechanisms," *Pesticide Biochemistry and Physiology*, 2004, vol. 78, pp. 21-30.

Zelaya, I., et al., "Evolved resistance to acetolactate synthase-inhibiting herbicides in common sunflower (*Helianthus annuus*), giant ragweed (*Ambrosia trifida*), and shattercane (*Sorghum bicolor*) in Iowa," *Weed Science*, 2004, vol. 52, pp. 538-548.

Al-Khatib, K., et al., "Survey of Common Sunflower (*Helianthus annuus*) Resistance to ALS-inhibiting Herbicides in Northeast Kansas". Proceedings of the 21st Sunflower Research Workshop. National Sunflower Association, pp. 210-215; Bismark, ND (Jan. 14-15, 1999).

Al-Khatib, K., et al., "Imazethapyr resistance in common sunflower (*Helianthus annuus*)" Weed Science, 46:403-407 (1998).

Avila, L. A., et al., "Assessment of Acetolactate Synthase (ALS) tolerance to Imazethapyr in Red Rice Ecotypes (*Oryza* spp) and Imidazolinone Tolerant/Resistant Rice (*Oryza sativa*) Varietites". Pest Management Science, vol. 61, No. 2, pp. 171-178 (2005).

Ayyadevara, S., et al., "Discrimination of Primer 3"—Nucleotide Mismatch by Tag DNA Polymerase during Polymerase Chain Reaction". Analytical Biochemistry, vol. 284, pp. 11-18 (2000); Academic Press.

Barbosa Filho, M.P., et al., "Upland Rice Production in Brazil," Better Crops International, vol. 16, pp. 43-47, Special Supplement, May 2002.

(56) References Cited

OTHER PUBLICATIONS

Barrett, M., "Protection of Grass Crops from Sulfonylurea and Imidazolinone Toxicity". Crop Safeners for Herbicides, pp. 195-220 (1990); Academic Press Inc.
Bennett, Full Complement of Clearfield rice varieties: 2009, Delta Farm Press, Feb. 25, 2008 [online]. [Retrieved on Jan. 3, 2010]. Retrieved from the internet: <URL: http://deltafarmpress.com/rice/clearfield-update-0225/> p. 1, paragraph 14, in 1.
Bernasconi, P., et al., "A Naturally Occurring Point Mutation Confers Broad Range Tolerance to Herbicides That Target Acetolactate Synthase". Journal of Biological Chemistry, vol. 270, No. 29, pp. 17381-17385 (1995).
Boutsalis, P., et al., "Molecular Basis of Resistance to Acetolactate Synthase-Inhibiting Herbicides in *Sisymbrium orientale* and *Bassica tournefortii*". Pesticide Science, vol. 55, pp. 507-516 (1999).
Brown, M., et al., "Hydrolytic Activation versus Oxidative Degradation of Assert Herbicide, an Imidazolinone Aryl-carboxylate, in Susceptible Wild Oat versus Tolerant Corn and Wheat". Pesticide Biochemistry and Physiology, vol. 27, pp. 24-29 (1987); Academic Press Inc.
Buchheim, J., et al., "Maturation of Soybean Somatic Embryos and the Transition to Plantlet Growth". Plant Physiol., vol. 89, pp. 768-775 (1989).
Chamovitz, D., et al., "The Molecular Basis of Resistance to the Herbicide Norflurazon". Plant Moleculat Biology, vol. 16, pp. 967-974 (1991).
Chang, et al., "Herbicide-resistant forms of *Arabidopsis thaliana* acetohydroxyacid synthase: characterization of the catalytic properties and sensitivity to inhibitors of four defined mutants". Biochem. J., vol. 333, pp. 765-777 (1998).
Chong, C, et al., "Amino Acid Residues Conferring Herbicide Tolerance in Tobacco Acetolactate Synthase". Biochemical and Biophysical Research Communications, vol. 279, pp. 462-467 (2000); Academic Press Inc.
De Battista, Juan Jose. "Rice Management and Fertilization in Entre Rios Province"; Special Supplement Publication; Better Crops International, vol. 16, pp. 40-42 (May 2002).
Delrio-Lafreniere Sa et al., "Simultaneous allele-specific amplification: a strategy using modified primer-template mismatches for SNP detection—application to prothrombin 20210A (factor II) and factor V Leiden (1691A) gene mutations". Molecular Diagnostics, vol. 6, No. 3, pp. 201-209 (2001).
Doberman, A., et al., "Rice Straw Management", Better Crops International, vol. 16, pp. 7-11, Special Supplementa, May 2002.
Duggleby, R. G., et al., "Acetohydroxyacid Synthase". Journal of Biochemistry and Molecular Biology, Korean Society for Biochemistry and Molecular Biology, KR, vol. 33, No. 1, pp. 1-36 (Jan. 2000).
Duggleby, R., "Identification of an Acetolactate Synthase Small Subunit Gene in Two Eukaryotes". Gene, vol. 190, pp. 245-249 (1997).
Espinosa, Jose, "Rice Nutrition Management in Latin America," Better Crops International, vol. 16, pp. 36-39, (2002).
Fairhurst, et al., "Rice in the Global Food Supply," Better Crops International, vol. 16, pp. 3-6, Special Supplement May 2002.
Finer, J., et al., "Apical Proliferation of Embryogenic Tissue of Soybean [*Glycine max* (L.) Merrill]". Plant Cell Reports, vol. 7, pp. 238-241 (1988).
Finer, J.J., et al., "Development of an Embryogenic Suspension Culture of Soybean (*Glycine max*Merill)". Plant Cell, Tissue, and Organ Culture, vol. 15, pp. 125-146 (1988). Kluwer Academic Publishers, Dordrecht Netherlands.
Gallie, D. R., et al., "The Regulation of Gene Expression in Transformed Maize Aleurone and Endosperm Protoplasts: Analysis of Promoter Activity, Intron Enhancement, and mRNA Untranslated Regions on Expression". Plant Physiol., vol. 106, ppn 929-939 (1994).
Gang, Pan et al., "Map-based cloning of a novel rice cytochrome P450 gene CYP81A6 that confers resistance to two different classes of herbicides". Plant Molecular Biology, Kluwer Academic Publishers, DO, vol. 61, No. 6, pp. 933-943 (Aug. 2006).

Hattori, J., et al., "An Acetohydroxyacid Synthase Mutant Reveals a Single Site Involved in Multiple Herbicide Resistance". Molecular and General Genetics, vol. 246, pp. 419-425 (1995); Springer Verlag, Berlin, Germany.
Hattori, J., et al., "Multiple resistance to sulfonylureas and imidazolinones conferred by an acetohydroxyacid synthase gene with separate mutation for selective resistance". Molecular Genetics, vol. 232, pp. 167-173 (1992).
Hershey, H., et al., "Cloning and Functional Expression of the Small Subunit of Acetolactate Synthase from *Nicotiana plumbaginifolia*". Plant Molecular Biology, vol. 40, pp. 795-806 (1999); Kluwer Academic Publishers; Netherlands.
Inui, Hideyuki, et al., "Herbicide resistance in transgenic plants with mammalian P450 monooxygenase genes". Pest Management Science, vol. 61, No. 3, pp. 286-291 (Mar. 2005).
Jacq, B., et al., "Efficient Production of Uniform Plants from Cotyledon Explants of Sugarbeets (*Beta vulgaris* L.)". Plant Breeding, vol. 110, pp. 185-191 (1993).
Ji-Yun, J., et al., "Rice Production and Fertilization in China," Better Crops International, vol. 16, pp. 26-29, Special Supplement, May 2002.
Kadaru, S., et al., "Development and application of allele-specific PCR assays for imazethapyr resistance in rice (*Oryza sativa*)," Euphytica, vol. 160, pp. 431-438, (2008).
Kaneda, Y., et al., Combination of Thidiazuron and Basal Media with Low Salt Concentrations Increases the Frequency of Shoot Organogenesis in Soybeans [*Glycine max* (I.) Merr.]. Plant Cell Reports, vol. 17, pp. 8-12 (1997).
Kolkman, J. M., et al., "Acetohydroxyacid synthase mutations conferring resistance to imidazolinone or sulfonylurea herbicides in sunflower". Theor. Appl. Genet, vol. 109, pp. 1147-1159 (2004).
Koziel, M. G., et al., "Optimizing expression of transgenes with an emphasis on post-transcriptional events". Plant Molecular Biology, vol. 32, pp. 393-405 (1996).
Kulshreshtha, S., et al., "Direct Somatic Embryogenesis and Plant Regeneration from Mature Sugarbeet (*Beta vulgaris* L.) Zygotic Cotyledons". Plant Growth Regulation, vol. 22, pp. 87-92 (1997).
Lai, F. M., et al., "Scale-up of Somatic Embryogenesis in Alfalfa (*Medicago sativa* L.) I Subculture and Indirect Secondary Somatic Embryogenesis". Plant Cell, Tissue and Organ Culture, vol. 37, pp. 151-158 (1994).
Lee, I., et al., "Guidelines for incorporating non-perfectly matched oligonucleotides into target-specific hybridization probes for DNA microarray". Nucleic Acids Research, vol. 32, pp. 681-690 (2004); Oxford University Press.
Lee, Y., et al., "Effect of Mutagenesis at Serine 653 of *Arabidopsis thaliana* Acetohydroxyacid Synthase on the Sensitivity to Imidazolinone and Sulfonylurea Herbicides". FEBS Letters, vol. 452, pp. 341-345 (1999); Federation of European Biochemical Societies.
Lee, Y., et al., "Identification of the Regulatory Subunit of *Arabidopsis thaliana* Acetohydroxyacid Synthase and Reconstitution with its Catalytic Subunit". Biochemistry, vol. 40, pp. 6836-6844 (2001).
Lenzner, S., et al., "Plant Regeneration form Protoplasts of Sugar Beet (*Beta vulgaris*)". Physiologia Plantarum, vol. 94, pp. 342-350 (1995); Denmark.
Li D., et al., "A mutation at the Ala122 position of acetohydroxyacid synthase (AHAS) located on chromosome 6D of wheat: improved resistance to imidazolinone and a faster assay for marker assisted selection". Mol. Breeding, vol. 22, pp. 217-225 (2008).
Li, L.,. et al., "An improved rice transformation system using the biolistic method". Plant Cell Reports, vol. 12, pp. 250-255 (1993).
Liu, W., et al., "Somatic Embryo Cycling: Evaluation of a Novel Transformation and Assay System for Seed-Specific Gene Expression in Soybean". Plant Cell, Tissue and Organ Culture, vol. 47, pp. 33-42 (1996).
Mazur, et al., "Isolation and Characterization of Plant Genes Coding for Acetolactate Synthase, the Target Enzyme for Two Classes of Herbicides". Plant Physiol., vol. 85, pp. 1110-1117 (1987).
McGranahan, G. H., et al., "Improved Efficiency of the Walnut Somatic Embryo Gene Transfer System". Plant Cell Reports, vol. 8, pp. 512-516 (1990).

(56) References Cited

OTHER PUBLICATIONS

Miki et al., "Transformation of *Brassica napus* canola cultivars with *Arabidopsis thaliana* Acetohydroxyacid Synthase Genes and Analysis of Herbicide Resistance". Theor. Appl. Genet., vol. 80, pp. 449-458 (1990).

Miller, J.F., et al., "Registration of Two Oilseed Sunflower Genetic Stocks, SURES-1 and SURES-2 Resistant to Tribenuron Herbicide," Crop Science Society of America, vol. 44 No. 3, pp. 1037-1038 (May 2004).

Milliman, L. D., et al., "Characterization of two biotypes of imidazolinone-resistant eastern black nightshade (*Solanum ptycanthum*)". Weed Science, vol. 51, pp. 139-144 (2003).

Moghaddam, B., et al., "The Effect of In Planta TIBA and Proline Treatment on Somatic Embryogenesis of Sugar Beet (*Beta vulgaris* L.)". Euphytica, vol. 112, No. 2, pp. 151-156 (Jan. 2000).

Mutert, E., et al., "Developments in Rice Production in Southeast Asia", Better Crops International, vol. 15, pp. 12-17, Special Supplement, May 2002.

Newhouse, K., et al., "Mutations in corn (*Zea mays* L) Conferring Resistance to Imidazolinone Herbicides". Theor. Appl. Genet., vol. 83, pp. 65-70 (1991); Springer-Verlag.

Newhouse, K., et al., "Tolerance to Imidazolinone Herbicides in Wheat". Plant Physiology, vol. 100, pp. 882-886 (1992).

Nielsen, J. M., et al., "Synergism of Thidiazuron and Benzyladenine in Axillary Shoot Formation Depends on Sequence of Application in *Miscanthus* X *ogiformis* 'Giganteus'". Plant Cell, Tissue and Organ Culture, vol. 41, pp. 165-170 (1995).

Odell, et al., "Comparision of Increased Expression of Wild-Type and Herbicide-Resistant Acetolactate Synthase Genes in Transgenic Plants, and Indication of Posttranscriptional Limitation on Enzyme Activity". Plant Physiol., vol. 94, pp. 1647-1654 (1990).

Ott, K., et al., "Rational Molecular Design and Genetic Engineering of Herbicide Resistant Crops by Structure Modeling and Site-directed Mutagenesis of Acetohydroxyacid Synthase". J. Mol. Biol., vol. 263, pp. 359-368 (1996); Academic Press Limited.

Owens, L. D., et al., "Sugarbeet Leaf Disc Culture: An Improved Procedure for Inducing Morphogenesis". Plant Cell, Tissue and Organ Culture, vol. 31, pp. 195-201 (1992).

Pettersson, M., et al., "Molecular haplotype determination using allele-specific PCR and Pyrosequencing technology". Genomics, vol. 82, pp. 390-396 (2003); Reed Elsevier Science.

Pozniak, C. J., et al., "Physiological and Molecular Characterization of Mutation-Derived Imidazolinone Resistance in Spring Wheat". Crop Science, vol. 44, No. 4, pp. 1434-1443 (2004).

Ray et al., "Mutant Acetolactate Synthase Gene is an Efficient in vitro Selectable Marker for the Genetic Transformation of *Brassica juncea* (Oilseed Mustard)". Journal of Plant Physiology, vol. 161, pp. 1079-1083 (2004).

Repellin, et al., "Genetic Enrichment of Cereal Crops via Alien Gene Transfer: New Challenges". Plant Cell, Tissue and Organ Culture, vol. 64, pp. 159-183 (2001).

Roesler, K., et. al., "Targeting of the *Arabidopsis* homomeric acetyl-coenzyme A carboxylase to plastids of rapeseeds". Plant Physiology, vol. 113, pp. 75-81 (1997).

Roussey, I., et al., "In Planta 2,3,5 Triiodobenzoic Acid Treatment Promotes High Frequency and Routine On Vitro Regeneration of Sugarbeet (*Beta vulgaris* L.) Plant". Plant Cell Reports, vol. 16, pp. 142-146 (1996).

Rutledge, et al. Molecular and General Genetics, vol. 229, pp. 31-40 (1991).

Sathasivan, K., et al., "Molecular Basis of Imidazolinone Herbicide Resistance in *Arabidopsis thaliana* var. Columbia". Plant Physiology, vol. 97, pp. 1044-1050 (1991).

Sato, S., et al., "Stable Transformation Via Particle Bombardment in Two Different Soybean Regeneration Systems". Plant Cell Reports, vol. 12, pp. 408-413 (1993).

Saxena et al., "Herbicide Resistance in *Datura innoxia* ". Plant Physiol., vol. 86, pp. 863-867 (1988).

Schmitzer, P. R., et al., "Lack of Cross-Resistance of Imazaquin-Resistant *Xanthium strumarium* Acetolactate Synthase to Flumetsulam and Chlorimuron". Plant Physiol, vol. 103, pp. 281-283 (1993).

Sella, C., et al., "Subunit Association in Acetohydroxy Acid Synthase Isozyme III". Journal of Bacteriology, vol. 175, No. 17, pp. 5339-5343 (Sep. 1993).

Sha, X.Y., "Field Evaluation of Imidazolinone-Tolerant Clearfield Rice (*Oryza sativa* L.) at Nine Louisiana Locations," CropScience, vol. 47, pp. 1177-1185 (2007).

Shaner, D., et al., "Imidazolinones: Potent Inhibitors of Acetohydroxyacid Synthase". Plant Physiol, vol. 76, pp. 545-546 (1984).

Shivrain, V.K., et al., "Gene flow between Clearfield™ rice and red rice," ScienceDirect, Crop Protection, vol. 26 pp. 349-356, (2007).

Snyder, C.S., et al., "Rice Production in the United States—An Overview," Better Crops International, vol. 16, pp. 30-35, Special Supplement, May 2002.

Stein, N., et al., "A new DNA extraction method for high-throughput marker analysis in a large-genome species such as *Triticum aestivum*". Plant Breeding, vol. 120, pp. 354-356 (2001).

Swanson, E., et al., "Microspore Mutagenesis and Selection: Canola Plants with Field Tolerance to the Imidazolinones". Theor Appl Genet, vol. 96, pp. 525-530 (1989); Springer-Verlag.

Tan et al., "Herbicidal Inhibitors of Amino Acid Biosynthesis and Herbicide-Tolerant Crops". Amino Acids, vol. 30, pp. 195-204 (2006).

Tan, S., et al., "Imidazolinone-Tolerant Crops: History, Current Status and Future". Pest Managament Science, vol. 61, No. 3, pp. 246-257 (2005).

Tenning, Paul, et al., "Somatic Embryo genesis from zygotic embryos of sugar beet *Beta vulgaris*". Plant Science, vol. 81, pp. 103-109 (1992).

Tiwari, K.N., "Rice Production and Nutrient Management in India," Better Crops International, vol. 16, pp. 18-22, Special Supplement, May 2002.

Tranel, P. J., et al., "Resistance of Weeds to ALS-Inhibiting Herbicides: What Have We Learned?". Weed Science, Weed Science Society of America, Champaign, IL (US), vol. 50, No. 6, pp. 700-712 (Nov. 2002).

Wagner, J., et al., "Identification of ALS-inhibitor-resistant *Amaranthus* biotypes using polymerase chain reaction amplification of . . . ". Weed Research, vol. 42, pp. 280-286 (2002).

Warner, Thomas G., "Sweet success with tethered enzyme catalysis". Nature Biotechnology, vol. 16, pp. 720-721 (Aug. 1998).

Weinstock, et al., "Properties of Subcloned Subunits of Bacterial Acetohydroxy Acid Synthases". Journal of Bacteriology, vol. 174, No. 17, pp. 5560-5556 (Sep. 1992); American Society for Microbiology.

Werck-Reichhart, D., et al., "Cytochromes P450 for engineering herbicide tolerance". Trends in Plant Science, Elsevier Science, Oxford, GB, vol. 5, No. 3, p. 116-123 (Mar. 2000).

Werle E., et al., "Convenient single-step, one tube purification of PCR products for direct sequencing". Nucleic Acids Research, vol. 22, No. 20, pp. 4354-4355 (1994).

White, A. D., et al., "Common sunflower resistance to acetolactate synthase-inhibiting herbicides". Weed Science, vol. 50, pp. 432-437 (2002).

White, A. D., et al., "Isolation of Acetolactate Synthase Homologs in Common Sunflowers". Weed Science, Weed Science Society of America, Champaign, IL, vol. 51, No. 6, pp. 845-853 (Nov. 6, 2003).

Wiersma, C., et al., "Isolation, Expression and Phylogenetic Inheiritance of an Acetolactate Synthase Gene from *Brassica napus*". Mol. Gen. Genet., vol. 219, pp. 413-420 (1989).

Wright, M., et al., "A Simple Method for the Recovery of Multiple Fertile Plants from Individual Somatic Embryos of Soybean [*Glycine max* (L) Merrill]". In Vitro Cell Dev Bio., vol. 27P, pp. 153-157 (Jul. 1991). Tissue Culture Association.

(56) References Cited

OTHER PUBLICATIONS

Wright, T. R., et al., "Cell Selection and Inheritance of Imidazolinone Resistance in Sugarbeet (*Beta vulgaris*)". Theor. Appl. Genet., vol. 96, pp. 612-620 (1998); Springer-Verlag.

Wu, D., et al., "Allele-specific enzymatic amplification of B-globin genomic DNA for diagnosis of sickle cell anemia". Proceedings of the National Academy of Sciences, vol. 86, pp. 2757-2760 (1989).

Yu Qin et al., "Tolerance to acetolactate synthase and acetyl-coenzyme A carboxylase inhibiting herbicides in *Vulpia bromoides* is conferred by two co-existing resistance mechanisms". Pesticide Biochemistry and Physiology, vol. 78, No. 1, pp. 21-30 (Jan. 2004).

Zhang, W., et al., "Genetic and agronomic analyses of red rice—Clearfield hybrids and their progeny produced from natural and controlled crosses," Euphytica, vol. 164, pp. 659-668 (2008).

Zhu et al., "Engineering herbicide-resistant maize using chimeric RNA/DNA oligonucleotides". Nature Biotechnology, vol. 18, pp. 555-558 (2000).

Zhu, X. L., "Computational simulations of the interactions between acetyl-coenzyme-A carboxylase and clodinafop: resistance mechanism due to active and nonactive site mutations." J. Chem. Inf. Model., vol. 49, pp. 1936-1843 (Jul. 13, 2009).

\* cited by examiner

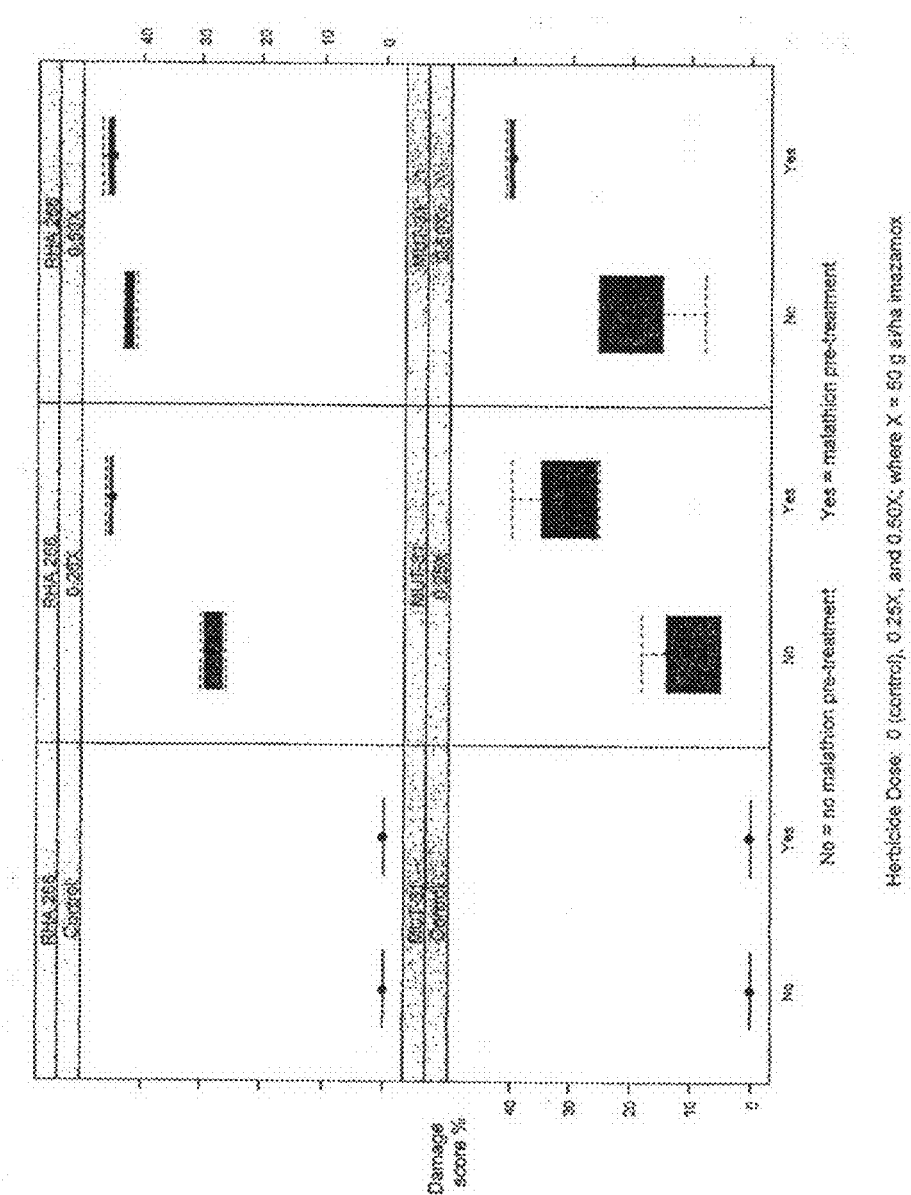

SEQUENCE LISTING

```
<160> NUMBER OF SEQ ID NOS: 6

<210> SEQ ID NO 1
<211> LENGTH: 1968
<212> TYPE: DNA
<213> ORGANISM: Helianthus annuus
<220> FEATURE:
<221> NAME/KEY: CDS
<222> LOCATION: (1)..(1968)

<400> SEQUENCE: 1 atg gcg gct cct ccc aac cct tcc atc tcc ttc aaa cca ccg tca ccc     48
Met Ala Ala Pro Pro Asn Pro Ser Ile Ser Phe Lys Pro Pro Ser Pro
1               5                   10                  15 gcc gcc gca ctg cca cca cgc tcc gcc ttc ctc ccc cgt ttc gca tta     96
Ala Ala Ala Leu Pro Pro Arg Ser Ala Phe Leu Pro Arg Phe Ala Leu
                20                  25                  30 ccc atc act tcc act acc caa aaa cga cac cgt ctt cac atc tcc aat    144
Pro Ile Thr Ser Thr Thr Gln Lys Arg His Arg Leu His Ile Ser Asn
            35                  40                  45 gtt ctc tcc gac tcc aaa tcc acc acc acc acc acc acc act caa        192
Val Leu Ser Asp Ser Lys Ser Thr Thr Thr Thr Thr Thr Thr Gln
        50                  55                  60 cga ccg tta ccg gtg cag cct ttt gtc tcc cgt tac gcg cca gat caa    240
Arg Pro Leu Pro Val Gln Pro Phe Val Ser Arg Tyr Ala Pro Asp Gln
65                  70                  75                  80 ccg aga aaa ggc gca gac gtg ttg gtg gaa gct ctg gaa cgg gaa ggt    288
Pro Arg Lys Gly Ala Asp Val Leu Val Glu Ala Leu Glu Arg Glu Gly
                85                  90                  95 gtc acc gac gtc ttc gcc tac ccc ggc ggc gcg tca atg gag atc cac    336
Val Thr Asp Val Phe Ala Tyr Pro Gly Gly Ala Ser Met Glu Ile His
                100                 105                 110 caa gct ctc acg cgc tca agc act atc cgc aat gtg ctc ccc cgt cac    384
Gln Ala Leu Thr Arg Ser Ser Thr Ile Arg Asn Val Leu Pro Arg His
            115                 120                 125 gaa cag ggc ggc gtg ttc gcc gcc gaa ggc tac gcg cgc gcc tcc ggt    432
Glu Gln Gly Gly Val Phe Ala Ala Glu Gly Tyr Ala Arg Ala Ser Gly
        130                 135                 140
```

```
                                       -continued ctt ccc ggc gtg tgt atc gcc act tcc ggt ccc gga gct acg aac cta      480
Leu Pro Gly Val Cys Ile Ala Thr Ser Gly Pro Gly Ala Thr Asn Leu
145                 150                 155                 160 gtt agt ggt ctt gct gac gcg ctg tta gac agt gtc ccc atg gtg gca      528
Val Ser Gly Leu Ala Asp Ala Leu Leu Asp Ser Val Pro Met Val Ala
            165                 170                 175 atc acc ggt caa gtt ccc cgg aga atg atc gga acc gat gcg ttt caa      576
Ile Thr Gly Gln Val Pro Arg Arg Met Ile Gly Thr Asp Ala Phe Gln
        180                 185                 190 gaa acc cca att gtt gag gta aca cgt tcg atc act aaa cat aat tat      624
Glu Thr Pro Ile Val Glu Val Thr Arg Ser Ile Thr Lys His Asn Tyr
    195                 200                 205 ctt gtg ttg gat gtt gag gat att ccc aga att gtt cgt gag gct ttt      672
Leu Val Leu Asp Val Glu Asp Ile Pro Arg Ile Val Arg Glu Ala Phe
210                 215                 220 tat ctt gcg agt tcg ggt cga ccc ggc ccg gtt ttg ata gat gta ccg      720
Tyr Leu Ala Ser Ser Gly Arg Pro Gly Pro Val Leu Ile Asp Val Pro
225                 230                 235                 240 aaa gat ata cag caa cag tta gtg gtg ccg aaa tgg gat gaa ccg atg      768
Lys Asp Ile Gln Gln Gln Leu Val Val Pro Lys Trp Asp Glu Pro Met
            245                 250                 255 agg tta ccg ggt tat ttg tct aga atg ccg aag cct caa tat gat ggg      816
Arg Leu Pro Gly Tyr Leu Ser Arg Met Pro Lys Pro Gln Tyr Asp Gly
        260                 265                 270 cat ttg gaa cag att gtt agg ttg gtg ggg gaa gcg aag agg ccg gtt      864
His Leu Glu Gln Ile Val Arg Leu Val Gly Glu Ala Lys Arg Pro Val
    275                 280                 285 ttg tat gtg ggt ggt ggg tgt ttg aat tcg gat gat gag ttg agg cgg      912
Leu Tyr Val Gly Gly Gly Cys Leu Asn Ser Asp Asp Glu Leu Arg Arg
290                 295                 300 ttt gtg gag ctt acg ggg att ccg gtt gcg agt act ttg atg ggg ctc      960
Phe Val Glu Leu Thr Gly Ile Pro Val Ala Ser Thr Leu Met Gly Leu
305                 310                 315                 320 gga gcg tac cct gct tcg agt gat ttg tcg ctt cat atg ctt ggg atg     1008
Gly Ala Tyr Pro Ala Ser Ser Asp Leu Ser Leu His Met Leu Gly Met
            325                 330                 335 cat ggt acg gtt tat gcg aat tat gcg gtt gat aag agt gat ttg ttg     1056
His Gly Thr Val Tyr Ala Asn Tyr Ala Val Asp Lys Ser Asp Leu Leu
        340                 345                 350 ctt gcg ttt ggg gtg cgg ttt gat gat cgt gtg acg ggg aag ctt gag     1104
Leu Ala Phe Gly Val Arg Phe Asp Asp Arg Val Thr Gly Lys Leu Glu
    355                 360                 365 gcg ttt gct agt agg gcg aag att gtt cat att gat att gat cct gct     1152
Ala Phe Ala Ser Arg Ala Lys Ile Val His Ile Asp Ile Asp Pro Ala
370                 375                 380 gaa att ggg aag aat aag cag cct cat gtg tcg att tgt ggt gat att     1200
Glu Ile Gly Lys Asn Lys Gln Pro His Val Ser Ile Cys Gly Asp Ile
385                 390                 395                 400 aag gtc gcg tta cag ggt ttg aac aag att ttg gag gaa aag aat tcg     1248
Lys Val Ala Leu Gln Gly Leu Asn Lys Ile Leu Glu Glu Lys Asn Ser
            405                 410                 415 gtg act aat ctt gat ttt tcg acc tgg aga aag gaa ttg gat gaa caa     1296
Val Thr Asn Leu Asp Phe Ser Thr Trp Arg Lys Glu Leu Asp Glu Gln
        420                 425                 430 aaa atg aag ttc ccg ttg agc ttt aaa acg ttt ggc gaa gcg att cct     1344
Lys Met Lys Phe Pro Leu Ser Phe Lys Thr Phe Gly Glu Ala Ile Pro
    435                 440                 445 cca cag tat gct att caa gtt ctt gat gag tta acg ggc ggg aat gca     1392
Pro Gln Tyr Ala Ile Gln Val Leu Asp Glu Leu Thr Gly Gly Asn Ala
450                 455                 460
```

```
                                                        -continued att att agc acc ggt gtc ggg caa cat cag atg tgg gct gct cag ttt    1440
Ile Ile Ser Thr Gly Val Gly Gln His Gln Met Trp Ala Ala Gln Phe
465                 470                 475                 480 tac aaa tac aac aaa cct aga caa tgg ctg acg tcg ggg gga cta ggg    1488
Tyr Lys Tyr Asn Lys Pro Arg Gln Trp Leu Thr Ser Gly Gly Leu Gly
                485                 490                 495 gca atg ggt ttc ggc ctg ccc gct gct atc ggg gcg gcc gtt gca aga    1536
Ala Met Gly Phe Gly Leu Pro Ala Ala Ile Gly Ala Ala Val Ala Arg
            500                 505                 510 cct gat gcg gta gta gtt gac atc gac ggt gac gga agc ttt atg atg    1584
Pro Asp Ala Val Val Val Asp Ile Asp Gly Asp Gly Ser Phe Met Met
        515                 520                 525 aat gtt caa gag tta gcc aca atc cgt gtt gaa aat ctg ccg gtt aag    1632
Asn Val Gln Glu Leu Ala Thr Ile Arg Val Glu Asn Leu Pro Val Lys
    530                 535                 540 att tta tta ctt aac aac cag cat ttg ggt atg gtg gtt cag tgg gag    1680
Ile Leu Leu Leu Asn Asn Gln His Leu Gly Met Val Val Gln Trp Glu
545                 550                 555                 560 gat cgg ttt tac aag gcg aat cgg gct cat acc tac tta gga aac ccg    1728
Asp Arg Phe Tyr Lys Ala Asn Arg Ala His Thr Tyr Leu Gly Asn Pro
                565                 570                 575 tca aaa gag tcg gaa ata ttc cct aac atg gtg aag ttt gct gaa gcc    1776
Ser Lys Glu Ser Glu Ile Phe Pro Asn Met Val Lys Phe Ala Glu Ala
            580                 585                 590 tgt gat atc ccg gct gct cga gtg acc caa aag gcg gat cta cga gca    1824
Cys Asp Ile Pro Ala Ala Arg Val Thr Gln Lys Ala Asp Leu Arg Ala
        595                 600                 605 gct att cag aag atg ttg gat aca ccc ggg cct tac ttg ttg gat gtg    1872
Ala Ile Gln Lys Met Leu Asp Thr Pro Gly Pro Tyr Leu Leu Asp Val
    610                 615                 620 att gtg ccg cat caa gaa cac gtg ttg ccc atg atc ccg gct ggc gga    1920
Ile Val Pro His Gln Glu His Val Leu Pro Met Ile Pro Ala Gly Gly
625                 630                 635                 640 ggt ttc tcg gat gtg atc acc gag ggt gat ggc aga acg aaa tat tga    1968
Gly Phe Ser Asp Val Ile Thr Glu Gly Asp Gly Arg Thr Lys Tyr
                645                 650                 655

<210> SEQ ID NO 2
<211> LENGTH: 655
<212> TYPE: PRT
<213> ORGANISM: Helianthus annuus

<400> SEQUENCE: 2

Met Ala Ala Pro Pro Asn Pro Ser Ile Ser Phe Lys Pro Pro Ser Pro
1               5                   10                  15

Ala Ala Ala Leu Pro Pro Arg Ser Ala Phe Leu Pro Arg Phe Ala Leu
            20                  25                  30

Pro Ile Thr Ser Thr Thr Gln Lys Arg His Arg Leu His Ile Ser Asn
        35                  40                  45

Val Leu Ser Asp Ser Lys Ser Thr Thr Thr Thr Thr Thr Thr Thr Gln
    50                  55                  60

Arg Pro Leu Pro Val Gln Pro Phe Val Ser Arg Tyr Ala Pro Asp Gln
65                  70                  75                  80

Pro Arg Lys Gly Ala Asp Val Leu Val Glu Ala Leu Glu Arg Glu Gly
                85                  90                  95

Val Thr Asp Val Phe Ala Tyr Pro Gly Gly Ala Ser Met Glu Ile His
            100                 105                 110

Gln Ala Leu Thr Arg Ser Ser Thr Ile Arg Asn Val Leu Pro Arg His
        115                 120                 125
```

```
Glu Gln Gly Gly Val Phe Ala Ala Glu Gly Tyr Ala Arg Ala Ser Gly
            130                 135                 140

Leu Pro Gly Val Cys Ile Ala Thr Ser Gly Pro Gly Ala Thr Asn Leu
145                 150                 155                 160

Val Ser Gly Leu Ala Asp Ala Leu Leu Asp Ser Val Pro Met Val Ala
                165                 170                 175

Ile Thr Gly Gln Val Pro Arg Arg Met Ile Gly Thr Asp Ala Phe Gln
            180                 185                 190

Glu Thr Pro Ile Val Glu Val Thr Arg Ser Ile Thr Lys His Asn Tyr
        195                 200                 205

Leu Val Leu Asp Val Glu Asp Ile Pro Arg Ile Val Arg Glu Ala Phe
210                 215                 220

Tyr Leu Ala Ser Ser Gly Arg Pro Gly Pro Val Leu Ile Asp Val Pro
225                 230                 235                 240

Lys Asp Ile Gln Gln Gln Leu Val Val Pro Lys Trp Asp Glu Pro Met
                245                 250                 255

Arg Leu Pro Gly Tyr Leu Ser Arg Met Pro Lys Pro Gln Tyr Asp Gly
            260                 265                 270

His Leu Glu Gln Ile Val Arg Leu Val Gly Glu Ala Lys Arg Pro Val
        275                 280                 285

Leu Tyr Val Gly Gly Gly Cys Leu Asn Ser Asp Asp Glu Leu Arg Arg
290                 295                 300

Phe Val Glu Leu Thr Gly Ile Pro Val Ala Ser Thr Leu Met Gly Leu
305                 310                 315                 320

Gly Ala Tyr Pro Ala Ser Ser Asp Leu Ser Leu His Met Leu Gly Met
                325                 330                 335

His Gly Thr Val Tyr Ala Asn Tyr Ala Val Asp Lys Ser Asp Leu Leu
            340                 345                 350

Leu Ala Phe Gly Val Arg Phe Asp Asp Arg Val Thr Gly Lys Leu Glu
        355                 360                 365

Ala Phe Ala Ser Arg Ala Lys Ile Val His Ile Asp Ile Asp Pro Ala
370                 375                 380

Glu Ile Gly Lys Asn Lys Gln Pro His Val Ser Ile Cys Gly Asp Ile
385                 390                 395                 400

Lys Val Ala Leu Gln Gly Leu Asn Lys Ile Leu Glu Glu Lys Asn Ser
                405                 410                 415

Val Thr Asn Leu Asp Phe Ser Thr Trp Arg Lys Glu Leu Asp Glu Gln
            420                 425                 430

Lys Met Lys Phe Pro Leu Ser Phe Lys Thr Phe Gly Glu Ala Ile Pro
        435                 440                 445

Pro Gln Tyr Ala Ile Gln Val Leu Asp Glu Leu Thr Gly Gly Asn Ala
450                 455                 460

Ile Ile Ser Thr Gly Val Gly Gln His Gln Met Trp Ala Ala Gln Phe
465                 470                 475                 480

Tyr Lys Tyr Asn Lys Pro Arg Gln Trp Leu Thr Ser Gly Gly Leu Gly
                485                 490                 495

Ala Met Gly Phe Gly Leu Pro Ala Ala Ile Gly Ala Ala Val Ala Arg
            500                 505                 510

Pro Asp Ala Val Val Val Asp Ile Asp Gly Asp Gly Ser Phe Met Met
        515                 520                 525

Asn Val Gln Glu Leu Ala Thr Ile Arg Val Glu Asn Leu Pro Val Lys
530                 535                 540
```

```
Ile Leu Leu Leu Asn Asn Gln His Leu Gly Met Val Val Gln Trp Glu
545                 550                 555                 560

Asp Arg Phe Tyr Lys Ala Asn Arg Ala His Thr Tyr Leu Gly Asn Pro
                565                 570                 575

Ser Lys Glu Ser Glu Ile Phe Pro Asn Met Val Lys Phe Ala Glu Ala
            580                 585                 590

Cys Asp Ile Pro Ala Ala Arg Val Thr Gln Lys Ala Asp Leu Arg Ala
        595                 600                 605

Ala Ile Gln Lys Met Leu Asp Thr Pro Gly Pro Tyr Leu Leu Asp Val
    610                 615                 620

Ile Val Pro His Gln Glu His Val Leu Pro Met Ile Pro Ala Gly Gly
625                 630                 635                 640

Gly Phe Ser Asp Val Ile Thr Glu Gly Asp Gly Arg Thr Lys Tyr
                645                 650                 655

<210> SEQ ID NO 3
<211> LENGTH: 655
<212> TYPE: PRT
<213> ORGANISM: Helianthus annuus

<400> SEQUENCE: 3

Met Ala Ala Pro Pro Asn Pro Ser Ile Ser Phe Lys Pro Pro Ser Pro
1               5                   10                  15

Ala Ala Ala Leu Pro Pro Arg Ser Ala Phe Leu Pro Arg Phe Ala Leu
                20                  25                  30

Pro Ile Thr Ser Thr Thr Gln Lys Arg His Arg Leu His Ile Ser Asn
            35                  40                  45

Val Leu Ser Asp Ser Lys Ser Thr Thr Thr Thr Thr Thr Thr Thr Gln
50                  55                  60

Arg Pro Leu Pro Val Gln Pro Phe Val Ser Arg Tyr Ala Pro Asp Gln
65                  70                  75                  80

Pro Arg Lys Gly Ala Asp Val Leu Val Glu Ala Leu Glu Arg Glu Gly
                85                  90                  95

Val Thr Asp Val Phe Ala Tyr Pro Gly Gly Ala Ser Met Glu Ile His
                100                 105                 110

Gln Ala Leu Thr Arg Ser Ser Thr Ile Arg Asn Val Leu Pro Arg His
            115                 120                 125

Glu Gln Gly Gly Val Phe Ala Ala Glu Gly Tyr Ala Arg Ala Ser Gly
        130                 135                 140

Leu Pro Gly Val Cys Ile Ala Thr Ser Gly Pro Gly Ala Thr Asn Leu
145                 150                 155                 160

Val Ser Gly Leu Ala Asp Ala Leu Leu Asp Ser Val Pro Met Val Ala
                165                 170                 175

Ile Thr Gly Gln Val Pro Arg Arg Met Ile Gly Thr Asp Ala Phe Gln
            180                 185                 190

Glu Thr Pro Ile Val Glu Val Thr Arg Ser Ile Thr Lys His Asn Tyr
        195                 200                 205

Leu Val Leu Asp Val Glu Asp Ile Pro Arg Ile Val Arg Glu Ala Phe
    210                 215                 220

Tyr Leu Ala Ser Ser Gly Arg Pro Gly Pro Val Leu Ile Asp Val Pro
225                 230                 235                 240

Lys Asp Ile Gln Gln Gln Leu Val Val Pro Lys Trp Asp Glu Pro Met
                245                 250                 255

Arg Leu Pro Gly Tyr Leu Ser Arg Met Pro Lys Pro Gln Tyr Asp Gly
            260                 265                 270
```

His Leu Glu Gln Ile Val Arg Leu Val Gly Glu Ala Lys Arg Pro Val
        275                 280                 285

Leu Tyr Val Gly Gly Cys Leu Asn Ser Asp Asp Glu Leu Arg Arg
    290                 295                 300

Phe Val Glu Leu Thr Gly Ile Pro Val Ala Ser Thr Leu Met Gly Leu
305                 310                 315                 320

Gly Ala Tyr Pro Ala Ser Ser Asp Leu Ser Leu His Met Leu Gly Met
                325                 330                 335

His Gly Thr Val Tyr Ala Asn Tyr Ala Val Asp Lys Ser Asp Leu Leu
            340                 345                 350

Leu Ala Phe Gly Val Arg Phe Asp Asp Arg Val Thr Gly Lys Leu Glu
    355                 360                 365

Ala Phe Ala Ser Arg Ala Lys Ile Val His Ile Asp Ile Asp Pro Ala
    370                 375                 380

Glu Ile Gly Lys Asn Lys Gln Pro His Val Ser Ile Cys Gly Asp Ile
385                 390                 395                 400

Lys Val Ala Leu Gln Gly Leu Asn Lys Ile Leu Glu Glu Lys Asn Ser
                405                 410                 415

Val Thr Asn Leu Asp Phe Ser Thr Trp Arg Lys Glu Leu Asp Glu Gln
            420                 425                 430

Lys Met Lys Phe Pro Leu Ser Phe Lys Thr Phe Gly Glu Ala Ile Pro
    435                 440                 445

Pro Gln Tyr Ala Ile Gln Val Leu Asp Glu Leu Thr Gly Gly Asn Ala
    450                 455                 460

Ile Ile Ser Thr Gly Val Gly Gln His Gln Met Trp Ala Ala Gln Phe
465                 470                 475                 480

Tyr Lys Tyr Asn Lys Pro Arg Gln Trp Leu Thr Ser Gly Gly Leu Gly
                485                 490                 495

Ala Met Gly Phe Gly Leu Pro Ala Ala Ile Gly Ala Ala Val Ala Arg
            500                 505                 510

Pro Asp Ala Val Val Asp Ile Asp Gly Asp Gly Ser Phe Met Met
    515                 520                 525

Asn Val Gln Glu Leu Ala Thr Ile Arg Val Glu Asn Leu Pro Val Lys
    530                 535                 540

Ile Leu Leu Leu Asn Asn Gln His Leu Gly Met Val Val Gln Trp Glu
545                 550                 555                 560

Asp Arg Phe Tyr Lys Ala Asn Arg Ala His Thr Tyr Leu Gly Asn Pro
                565                 570                 575

Ser Lys Glu Ser Glu Ile Phe Pro Asn Met Val Lys Phe Ala Glu Ala
            580                 585                 590

Cys Asp Ile Pro Ala Ala Arg Val Thr Gln Lys Ala Asp Leu Arg Ala
    595                 600                 605

Ala Ile Gln Lys Met Leu Asp Thr Pro Gly Pro Tyr Leu Leu Asp Val
    610                 615                 620

Ile Val Pro His Gln Glu His Val Leu Pro Met Ile Pro Ala Gly Gly
625                 630                 635                 640

Gly Phe Ser Asp Val Ile Thr Glu Gly Asp Gly Arg Thr Lys Tyr
                645                 650                 655

<210> SEQ ID NO 4
<211> LENGTH: 1968
<212> TYPE: DNA
<213> ORGANISM: Helianthus annuus

```
<220> FEATURE:
<221> NAME/KEY: CDS
<222> LOCATION: (1)..(1968)

<400> SEQUENCE: 4 atg gcg gct cct ccc aac cct tcc atc tcc ttc aaa cca ccg tca ccc      48
Met Ala Ala Pro Pro Asn Pro Ser Ile Ser Phe Lys Pro Pro Ser Pro
1               5                   10                  15 gcc gcc gca ctg cca cca cgc tcc gcc ttc ctc ccc gtt ttc gca tta      96
Ala Ala Ala Leu Pro Pro Arg Ser Ala Phe Leu Pro Arg Phe Ala Leu
                20                  25                  30 ccc atc act tcc act acc caa aaa cga cac cgt ctt cac atc tcc aat     144
Pro Ile Thr Ser Thr Thr Gln Lys Arg His Arg Leu His Ile Ser Asn
            35                  40                  45 gtt ctc tcc gac tcc aaa tcc acc acc acc acc acc acc act caa         192
Val Leu Ser Asp Ser Lys Ser Thr Thr Thr Thr Thr Thr Thr Gln
50                  55                  60 cga ccg tta ccg gtg cag cct ttt gtc tcc cgt tac gcg cca gat caa     240
Arg Pro Leu Pro Val Gln Pro Phe Val Ser Arg Tyr Ala Pro Asp Gln
65                  70                  75                  80 ccg aga aaa ggc gca gac gtg ttg gtg gaa gct ctg gaa cgg gaa ggt     288
Pro Arg Lys Gly Ala Asp Val Leu Val Glu Ala Leu Glu Arg Glu Gly
                85                  90                  95 gtc acc gac gtc ttc gcc tac ccc ggc ggc gcg tca atg gag atc cac     336
Val Thr Asp Val Phe Ala Tyr Pro Gly Gly Ala Ser Met Glu Ile His
            100                 105                 110 caa gct ctc acg cgc tca agc act atc cgc aat gtg ctc ccc cgt cac     384
Gln Ala Leu Thr Arg Ser Ser Thr Ile Arg Asn Val Leu Pro Arg His
        115                 120                 125 gaa cag ggc ggc gtg ttc gcc gcc gaa ggc tac gcg cgc gcc tcc ggt     432
Glu Gln Gly Gly Val Phe Ala Ala Glu Gly Tyr Ala Arg Ala Ser Gly
130                 135                 140 ctt ccc ggc gtg tgt atc gcc act tcc ggt ccc gga gct acg aac cta     480
Leu Pro Gly Val Cys Ile Ala Thr Ser Gly Pro Gly Ala Thr Asn Leu
145                 150                 155                 160 gtt agt ggt ctt gct gac gcg ctg tta gac agt gtc ccc atg gtg gca     528
Val Ser Gly Leu Ala Asp Ala Leu Leu Asp Ser Val Pro Met Val Ala
                165                 170                 175 atc acc ggt caa gtt ccc cgg aga atg atc gga acc gat gtg ttt caa     576
Ile Thr Gly Gln Val Pro Arg Arg Met Ile Gly Thr Asp Val Phe Gln
            180                 185                 190 gaa acc cca att gtt gag gta aca cgt tcg atc act aaa cat aat tat     624
Glu Thr Pro Ile Val Glu Val Thr Arg Ser Ile Thr Lys His Asn Tyr
        195                 200                 205 ctt gtg ttg gat gtt gag gat att ccc aga att gtt cgt gag gct ttt     672
Leu Val Leu Asp Val Glu Asp Ile Pro Arg Ile Val Arg Glu Ala Phe
210                 215                 220 tat ctt gcg agt tcg ggt cga ccc ggc ccg gtt ttg ata gat gta ccg     720
Tyr Leu Ala Ser Ser Gly Arg Pro Gly Pro Val Leu Ile Asp Val Pro
225                 230                 235                 240 aaa gat ata cag caa cag tta gtg gtg ccg aaa tgg gat gaa ccg atg     768
Lys Asp Ile Gln Gln Gln Leu Val Val Pro Lys Trp Asp Glu Pro Met
                245                 250                 255 agg tta ccg ggt tat ttg tct aga atg ccg aag cct caa tat gat ggg     816
Arg Leu Pro Gly Tyr Leu Ser Arg Met Pro Lys Pro Gln Tyr Asp Gly
            260                 265                 270 cat ttg gaa cag att gtt agg ttg gtg ggg gaa gcg aag agg ccg gtt     864
His Leu Glu Gln Ile Val Arg Leu Val Gly Glu Ala Lys Arg Pro Val
        275                 280                 285
```

-continued

| | | |
|---|---|---|
| ttg tat gtg ggt ggt ggg tgt ttg aat tcg gat gat gag ttg agg cgg<br>Leu Tyr Val Gly Gly Gly Cys Leu Asn Ser Asp Asp Glu Leu Arg Arg<br>290                               295                     300 | 912 |
| ttt gtg gag ctt acg ggg att ccg gtt gcg agt act ttg atg ggg ctc<br>Phe Val Glu Leu Thr Gly Ile Pro Val Ala Ser Thr Leu Met Gly Leu<br>305                               310                     315                  320 | 960 |
| gga gcg tac cct gct tcg agt gat ttg tcg ctt cat atg ctt ggg atg<br>Gly Ala Tyr Pro Ala Ser Ser Asp Leu Ser Leu His Met Leu Gly Met<br>325                           330                     335 | 1008 |
| cat ggt acg gtt tat gcg aat tat gcg gtt gat aag agt gat ttg ttg<br>His Gly Thr Val Tyr Ala Asn Tyr Ala Val Asp Lys Ser Asp Leu Leu<br>              340                     345                     350 | 1056 |
| ctt gcg ttt ggg gtg cgg ttt gat gat cgt gtg acg ggg aag ctt gag<br>Leu Ala Phe Gly Val Arg Phe Asp Asp Arg Val Thr Gly Lys Leu Glu<br>        355                     360                     365 | 1104 |
| gcg ttt gct agt agg gcg aag att gtt cat att gat att gat cct gct<br>Ala Phe Ala Ser Arg Ala Lys Ile Val His Ile Asp Ile Asp Pro Ala<br>370                               375                     380 | 1152 |
| gaa att ggg aag aat aag cag cct cat gtg tcg att tgt ggt gat att<br>Glu Ile Gly Lys Asn Lys Gln Pro His Val Ser Ile Cys Gly Asp Ile<br>385                               390                     395                  400 | 1200 |
| aag gtc gcg tta cag ggt ttg aac aag att ttg gag gaa aag aat tcg<br>Lys Val Ala Leu Gln Gly Leu Asn Lys Ile Leu Glu Glu Lys Asn Ser<br>                     405                     410                     415 | 1248 |
| gtg act aat ctt gat ttt tcg acc tgg aga aag gaa ttg gat gaa caa<br>Val Thr Asn Leu Asp Phe Ser Thr Trp Arg Lys Glu Leu Asp Glu Gln<br>              420                     425                     430 | 1296 |
| aaa atg aag ttc ccg ttg agc ttt aaa acg ttt ggc gaa gcg att cct<br>Lys Met Lys Phe Pro Leu Ser Phe Lys Thr Phe Gly Glu Ala Ile Pro<br>        435                     440                     445 | 1344 |
| cca cag tat gct att caa gtt ctt gat gag tta acg ggc ggg aat gca<br>Pro Gln Tyr Ala Ile Gln Val Leu Asp Glu Leu Thr Gly Gly Asn Ala<br>450                               455                     460 | 1392 |
| att att agc acc ggt gtc ggg caa cat cag atg tgg gct gct cag ttt<br>Ile Ile Ser Thr Gly Val Gly Gln His Gln Met Trp Ala Ala Gln Phe<br>465                               470                     475                  480 | 1440 |
| tac aaa tac aac aaa cct aga caa tgg ctg acg tcg ggc ggg cta ggg<br>Tyr Lys Tyr Asn Lys Pro Arg Gln Trp Leu Thr Ser Gly Gly Leu Gly<br>                     485                     490                     495 | 1488 |
| gca atg ggt ttc ggc ctg ccc gct gct atc ggg gcg gcc gtt gca aga<br>Ala Met Gly Phe Gly Leu Pro Ala Ala Ile Gly Ala Ala Val Ala Arg<br>        500                     505                     510 | 1536 |
| cct gat gcg gta gta gtt gac atc gac ggt gac gga agc ttt atg atg<br>Pro Asp Ala Val Val Val Asp Ile Asp Gly Asp Gly Ser Phe Met Met<br>515                               520                     525 | 1584 |
| aat gtt caa gag tta gcc aca atc cgt gtt gaa aat ctg ccg gtt aag<br>Asn Val Gln Glu Leu Ala Thr Ile Arg Val Glu Asn Leu Pro Val Lys<br>              530                     535                     540 | 1632 |
| att tta tta ctt aac aac cag cat ttg ggt atg gtg gtt cag tgg gag<br>Ile Leu Leu Leu Asn Asn Gln His Leu Gly Met Val Val Gln Trp Glu<br>545                               550                     555                  560 | 1680 |
| gat cgg ttt tac aag gcg aat cgg gct cat acc tac tta gga aac ccg<br>Asp Arg Phe Tyr Lys Ala Asn Arg Ala His Thr Tyr Leu Gly Asn Pro<br>                     565                     570                     575 | 1728 |
| tca aaa gag tcg gaa ata ttc cct aac atg gtg aag ttt gct gaa gcc<br>Ser Lys Glu Ser Glu Ile Phe Pro Asn Met Val Lys Phe Ala Glu Ala<br>        580                     585                     590 | 1776 |
| tgt gat atc ccg gct gct cga gtg acc caa aag gcg gat cta cga gca<br>Cys Asp Ile Pro Ala Ala Arg Val Thr Gln Lys Ala Asp Leu Arg Ala<br>595                               600                     605 | 1824 |

```
gct att cag aag atg ttg gat aca ccc ggg cct tac ttg ttg gat gtg    1872
Ala Ile Gln Lys Met Leu Asp Thr Pro Gly Pro Tyr Leu Leu Asp Val
        610             615                 620 att gtg ccg cat caa gaa cac gtg ttg ccc atg atc ccg gct ggc gga    1920
Ile Val Pro His Gln Glu His Val Leu Pro Met Ile Pro Ala Gly Gly
625                 630                 635                 640 ggt ttc tcg gat gtg atc acc gag ggt gat ggc aga acg aaa tat tga   1968
Gly Phe Ser Asp Val Ile Thr Glu Gly Asp Gly Arg Thr Lys Tyr
                645                 650                 655

<210> SEQ ID NO 5
<211> LENGTH: 655
<212> TYPE: PRT
<213> ORGANISM: Helianthus annuus

<400> SEQUENCE: 5

Met Ala Ala Pro Pro Asn Pro Ser Ile Ser Phe Lys Pro Pro Ser Pro
1               5                   10                  15

Ala Ala Ala Leu Pro Pro Arg Ser Ala Phe Leu Pro Arg Phe Ala Leu
            20                  25                  30

Pro Ile Thr Ser Thr Thr Gln Lys Arg His Arg Leu His Ile Ser Asn
        35                  40                  45

Val Leu Ser Asp Ser Lys Ser Thr Thr Thr Thr Thr Thr Thr Thr Gln
50                  55                  60

Arg Pro Leu Pro Val Gln Pro Phe Val Ser Arg Tyr Ala Pro Asp Gln
65                  70                  75                  80

Pro Arg Lys Gly Ala Asp Val Leu Val Glu Ala Leu Glu Arg Glu Gly
                85                  90                  95

Val Thr Asp Val Phe Ala Tyr Pro Gly Gly Ala Ser Met Glu Ile His
            100                 105                 110

Gln Ala Leu Thr Arg Ser Ser Thr Ile Arg Asn Val Leu Pro Arg His
        115                 120                 125

Glu Gln Gly Gly Val Phe Ala Ala Glu Gly Tyr Ala Arg Ala Ser Gly
    130                 135                 140

Leu Pro Gly Val Cys Ile Ala Thr Ser Gly Pro Gly Ala Thr Asn Leu
145                 150                 155                 160

Val Ser Gly Leu Ala Asp Ala Leu Leu Asp Ser Val Pro Met Val Ala
                165                 170                 175

Ile Thr Gly Gln Val Pro Arg Arg Met Ile Gly Thr Asp Val Phe Gln
            180                 185                 190

Glu Thr Pro Ile Val Glu Val Thr Arg Ser Ile Thr Lys His Asn Tyr
        195                 200                 205

Leu Val Leu Asp Val Glu Asp Ile Pro Arg Ile Val Arg Glu Ala Phe
    210                 215                 220

Tyr Leu Ala Ser Ser Gly Arg Pro Gly Pro Val Leu Ile Asp Val Pro
225                 230                 235                 240

Lys Asp Ile Gln Gln Gln Leu Val Val Pro Lys Trp Asp Glu Pro Met
                245                 250                 255

Arg Leu Pro Gly Tyr Leu Ser Arg Met Pro Lys Pro Gln Tyr Asp Gly
            260                 265                 270

His Leu Glu Gln Ile Val Arg Leu Val Gly Glu Ala Lys Arg Pro Val
        275                 280                 285

Leu Tyr Val Gly Gly Gly Cys Leu Asn Ser Asp Asp Glu Leu Arg Arg
    290                 295                 300

Phe Val Glu Leu Thr Gly Ile Pro Val Ala Ser Thr Leu Met Gly Leu
305                 310                 315                 320
```

```
Gly Ala Tyr Pro Ala Ser Ser Asp Leu Ser Leu His Met Leu Gly Met
            325                 330                 335

His Gly Thr Val Tyr Ala Asn Tyr Ala Val Asp Lys Ser Asp Leu Leu
        340                 345                 350

Leu Ala Phe Gly Val Arg Phe Asp Asp Arg Val Thr Gly Lys Leu Glu
            355                 360                 365

Ala Phe Ala Ser Arg Ala Lys Ile Val His Ile Asp Ile Asp Pro Ala
370                 375                 380

Glu Ile Gly Lys Asn Lys Gln Pro His Val Ser Ile Cys Gly Asp Ile
385                 390                 395                 400

Lys Val Ala Leu Gln Gly Leu Asn Lys Ile Leu Glu Glu Lys Asn Ser
            405                 410                 415

Val Thr Asn Leu Asp Phe Ser Thr Trp Arg Lys Glu Leu Asp Glu Gln
            420                 425                 430

Lys Met Lys Phe Pro Leu Ser Phe Lys Thr Phe Gly Glu Ala Ile Pro
        435                 440                 445

Pro Gln Tyr Ala Ile Gln Val Leu Asp Glu Leu Thr Gly Gly Asn Ala
        450                 455                 460

Ile Ile Ser Thr Gly Val Gly Gln His Gln Met Trp Ala Ala Gln Phe
465                 470                 475                 480

Tyr Lys Tyr Asn Lys Pro Arg Gln Trp Leu Thr Ser Gly Gly Leu Gly
            485                 490                 495

Ala Met Gly Phe Gly Leu Pro Ala Ala Ile Gly Ala Ala Val Ala Arg
                500                 505                 510

Pro Asp Ala Val Val Asp Ile Asp Gly Asp Gly Ser Phe Met Met
            515                 520                 525

Asn Val Gln Glu Leu Ala Thr Ile Arg Val Glu Asn Leu Pro Val Lys
530                 535                 540

Ile Leu Leu Leu Asn Asn Gln His Leu Gly Met Val Val Gln Trp Glu
545                 550                 555                 560

Asp Arg Phe Tyr Lys Ala Asn Arg Ala His Thr Tyr Leu Gly Asn Pro
            565                 570                 575

Ser Lys Glu Ser Glu Ile Phe Pro Asn Met Val Lys Phe Ala Glu Ala
        580                 585                 590

Cys Asp Ile Pro Ala Ala Arg Val Thr Gln Lys Ala Asp Leu Arg Ala
595                 600                 605

Ala Ile Gln Lys Met Leu Asp Thr Pro Gly Pro Tyr Leu Leu Asp Val
610                 615                 620

Ile Val Pro His Gln Glu His Val Leu Pro Met Ile Pro Ala Gly Gly
625                 630                 635                 640

Gly Phe Ser Asp Val Ile Thr Glu Gly Asp Gly Arg Thr Lys Tyr
            645                 650                 655

<210> SEQ ID NO 6
<211> LENGTH: 655
<212> TYPE: PRT
<213> ORGANISM: Helianthus annuus

<400> SEQUENCE: 6

Met Ala Ala Pro Pro Asn Pro Ser Ile Ser Phe Lys Pro Ser Pro
1               5                   10                  15

Ala Ala Ala Leu Pro Pro Arg Ser Ala Phe Leu Pro Arg Phe Ala Leu
            20                  25                  30

Pro Ile Thr Ser Thr Thr Gln Lys Arg His Arg Leu His Ile Ser Asn
        35                  40                  45
```

-continued

```
Val Leu Ser Asp Ser Lys Ser Thr Thr Thr Thr Thr Thr Thr Gln
 50                  55                  60

Arg Pro Leu Pro Val Gln Pro Phe Val Ser Arg Tyr Ala Pro Asp Gln
 65                  70                  75                  80

Pro Arg Lys Gly Ala Asp Val Leu Val Glu Ala Leu Glu Arg Glu Gly
                 85                  90                  95

Val Thr Asp Val Phe Ala Tyr Pro Gly Gly Ala Ser Met Glu Ile His
                100                 105                 110

Gln Ala Leu Thr Arg Ser Ser Thr Ile Arg Asn Val Leu Pro Arg His
            115                 120                 125

Glu Gln Gly Gly Val Phe Ala Ala Glu Gly Tyr Ala Arg Ala Ser Gly
130                 135                 140

Leu Pro Gly Val Cys Ile Ala Thr Ser Gly Pro Gly Ala Thr Asn Leu
145                 150                 155                 160

Val Ser Gly Leu Ala Asp Ala Leu Leu Asp Ser Val Pro Met Val Ala
                165                 170                 175

Ile Thr Gly Gln Val Pro Arg Arg Met Ile Gly Thr Asp Val Phe Gln
                180                 185                 190

Glu Thr Pro Ile Val Glu Val Thr Arg Ser Ile Thr Lys His Asn Tyr
            195                 200                 205

Leu Val Leu Asp Val Glu Asp Ile Pro Arg Ile Val Arg Glu Ala Phe
210                 215                 220

Tyr Leu Ala Ser Ser Gly Arg Pro Gly Pro Val Leu Ile Asp Val Pro
225                 230                 235                 240

Lys Asp Ile Gln Gln Gln Leu Val Val Pro Lys Trp Asp Glu Pro Met
                245                 250                 255

Arg Leu Pro Gly Tyr Leu Ser Arg Met Pro Lys Pro Gln Tyr Asp Gly
                260                 265                 270

His Leu Glu Gln Ile Val Arg Leu Val Gly Glu Ala Lys Arg Pro Val
            275                 280                 285

Leu Tyr Val Gly Gly Gly Cys Leu Asn Ser Asp Asp Glu Leu Arg Arg
290                 295                 300

Phe Val Glu Leu Thr Gly Ile Pro Val Ala Ser Thr Leu Met Gly Leu
305                 310                 315                 320

Gly Ala Tyr Pro Ala Ser Ser Asp Leu Ser Leu His Met Leu Gly Met
                325                 330                 335

His Gly Thr Val Tyr Ala Asn Tyr Ala Val Asp Lys Ser Asp Leu Leu
                340                 345                 350

Leu Ala Phe Gly Val Arg Phe Asp Asp Arg Val Thr Gly Lys Leu Glu
            355                 360                 365

Ala Phe Ala Ser Arg Ala Lys Ile Val His Ile Asp Ile Asp Pro Ala
370                 375                 380

Glu Ile Gly Lys Asn Lys Gln Pro His Val Ser Ile Cys Gly Asp Ile
385                 390                 395                 400

Lys Val Ala Leu Gln Gly Leu Asn Lys Ile Leu Glu Glu Lys Asn Ser
                405                 410                 415

Val Thr Asn Leu Asp Phe Ser Trp Arg Lys Glu Leu Asp Glu Gln
                420                 425                 430

Lys Met Lys Phe Pro Leu Ser Phe Lys Thr Phe Gly Glu Ala Ile Pro
            435                 440                 445

Pro Gln Tyr Ala Ile Gln Val Leu Asp Glu Leu Thr Gly Gly Asn Ala
450                 455                 460
```

```
Ile Ile Ser Thr Gly Val Gly Gln His Gln Met Trp Ala Ala Gln Phe
465             470             475             480

Tyr Lys Tyr Asn Lys Pro Arg Gln Trp Leu Thr Ser Gly Gly Leu Gly
            485             490             495

Ala Met Gly Phe Gly Leu Pro Ala Ala Ile Gly Ala Ala Val Ala Arg
            500             505             510

Pro Asp Ala Val Val Val Asp Ile Asp Gly Asp Gly Ser Phe Met Met
        515             520             525

Asn Val Gln Glu Leu Ala Thr Ile Arg Val Glu Asn Leu Pro Val Lys
        530             535             540

Ile Leu Leu Leu Asn Asn Gln His Leu Gly Met Val Val Gln Trp Glu
545             550             555             560

Asp Arg Phe Tyr Lys Ala Asn Arg Ala His Thr Tyr Leu Gly Asn Pro
            565             570             575

Ser Lys Glu Ser Glu Ile Phe Pro Asn Met Val Lys Phe Ala Glu Ala
            580             585             590

Cys Asp Ile Pro Ala Ala Arg Val Thr Gln Lys Ala Asp Leu Arg Ala
        595             600             605

Ala Ile Gln Lys Met Leu Asp Thr Pro Gly Pro Tyr Leu Leu Asp Val
    610             615             620

Ile Val Pro His Gln Glu His Val Leu Pro Met Ile Pro Ala Gly Gly
625             630             635             640

Gly Phe Ser Asp Val Ile Thr Glu Gly Asp Gly Arg Thr Lys Tyr
            645             650             655
```

HERBICIDE-RESISTANT SUNFLOWER PLANTS AND METHODS OF USE

CROSS-REFERENCE TO RELATED APPLICATIONS

This application is the U.S. National Stage of International Application PCT/EP2007/063737, filed Dec. 11, 2007, which was published by the International Bureau in English on Jun. 19, 2008 and designates the U.S., and which claims the benefit of U.S. Provisional Application No. 60/874,309 filed Dec. 12, 2006; both of which are hereby incorporated herein in their entirety by reference.

FIELD OF THE INVENTION

This invention relates to the field of agricultural biotechnology, particularly to herbicide-resistant sunflower plants and novel polynucleotide sequences that encode wild-type and herbicide-resistant sunflower acetohydroxyacid synthase large subunit proteins.

BACKGROUND OF THE INVENTION

Acetohydroxyacid synthase (AHAS; EC 4.1.3.18, also known as acetolactate synthase or ALS), is the first enzyme that catalyzes the biochemical synthesis of the branched chain amino acids valine, leucine and isoleucine (Singh (1999) "Biosynthesis of valine, leucine and isoleucine," in Plant Amino Acid, Singh, B. K., ed., Marcel Dekker Inc. New York, N.Y., pp. 227-247). AHAS is the site of action of five structurally diverse herbicide families including the sulfonylureas (LaRossa and Falco (1984) Trends Biotechnol. 2:158-161), the imidazolinones (Shaner et al. (1984) Plant Physiol. 76:545-546), the triazolopyrimidines (Subramanian and Gerwick (1989) "Inhibition of acetolactate synthase by triazolopyrimidines," in Biocatalysis in Agricultural Biotechnology, Whitaker, J. R. and Sonnet, P. E. eds., ACS Symposium Series, American Chemical Society, Washington, D.C., pp. 277-288), and the pyrimidyloxybenzoates (Subramanian et al. (1990) Plant Physiol. 94: 239-244). Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. Several examples of commercially available imidazolinone herbicides are PURSUIT® (imazethapyr), SCEPTER® (imazaquin) and ARSENAL® (imazapyr). Examples of sulfonylurea herbicides are chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, flazasulfuron, imazosulfuron, pyrazosulfuron ethyl and halosulfuron.

Due to their high effectiveness and low-toxicity, imidazolinone herbicides are favored for application by spraying over the top of a wide area of vegetation. The ability to spray a herbicide over the top of a wide range of vegetation decreases the costs associated with plant establishment and maintenance, and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone-resistant species of the desired vegetation in the spray over area.

Among the major agricultural crops, some leguminous species such as soybean are naturally resistant to imidazolinone herbicides due to their ability to rapidly metabolize the herbicide compounds (Shaner and Robinson (1985) Weed Sci. 33:469-471). Other crops such as corn (Newhouse et al. (1992) Plant Physiol. 100:882-886) and rice (Barrett et al. (1989) Crop Safeners for Herbicides, Academic Press, New York, pp. 195-220) are somewhat susceptible to imidazolinone herbicides. The differential sensitivity to the imidazolinone herbicides is dependent on the chemical nature of the particular herbicide and differential metabolism of the compound from a toxic to a non-toxic form in each plant (Shaner et al. (1984) Plant Physiol. 76:545-546; Brown et al., (1987) Pestic. Biochem. Physiol. 27:24-29). Other plant physiological differences such as absorption and translocation also play an important role in sensitivity (Shaner and Robinson (1985) Weed Sci. 33:469-471).

Plants resistant to imidazolinones, sulfonylureas, triazolopyrimidines, and pyrimidyloxybenzoates have been successfully produced using seed, microspore, pollen, and callus mutagenesis in Zea mays, Arabidopsis thaliana, Brassica napus (i.e., canola) Glycine max, Nicotiana tabacum, sugarbeet (Beta vulgaris) and Oryza sativa (Sebastian et al. (1989) Crop Sci. 29:1403-1408; Swanson et al., 1989 Theor. Appl. Genet. 78:525-530; Newhouse et al. (1991) Theor. Appl. Genet. 83:65-70; Sathasivan et al. (1991) Plant Physiol. 97:1044-1050; Mourand et al. (1993) J. Heredity 84:91-96; Wright and Penner (1998) Theor. Appl. Genet. 96:612-620; U.S. Pat. No. 5,545,822). In all cases, a single, partially dominant nuclear gene conferred resistance. Four imidazolinone-resistant wheat plants were also previously isolated following seed mutagenesis of Triticum aestivum L. cv. Fidel (Newhouse et al. (1992) Plant Physiol. 100:882-886). Inheritance studies confirmed that a single, partially dominant gene conferred resistance. Based on allelic studies, the authors concluded that the mutations in the four identified lines were located at the same locus. One of the Fidel cultivar resistance genes was designated FS-4 (Newhouse et al. (1992) Plant Physiol. 100:882-886).

Naturally occurring plant populations that were discovered to be resistant to imidazolinone and/or sulfonylurea herbicides have also been used to develop herbicide-resistant sunflower breeding lines. Recently, two sunflower lines that are resistant to a sulfonylurea herbicide were developed using germplasm originating from a wild population of common sunflower (Helianthus annuus) as the source of the herbicide-resistance trait (Miller and Al-Khatib (2004) Crop Sci. 44:1037-1038). Previously, White et al. ((2002) Weed Sci. 50:432-437) had reported that individuals from a wild population of common sunflower from South Dakota, U.S.A. were cross-resistant to an imidazolinone and a sulfonylurea herbicide. Analysis of a portion of the coding region of the acetohydroxyacid synthase large subunit (AHASL) genes of individuals from this population revealed a point mutation that results in an Ala-to-Val amino acid substitution in the sunflower AHASL protein that corresponds to $Ala_{205}$ in the wild-type Arabidopsis thaliana AHASL protein (White et al. (2003) Weed Sci. 51:845-853).

Computer-based modeling of the three dimensional conformation of the AHAS-inhibitor complex predicts several amino acids in the proposed inhibitor binding pocket as sites where induced mutations would likely confer selective resistance to imidazolinones (Ott et al. (1996) J. Mol. Biol. 263: 359-368). Wheat plants produced with some of these rationally designed mutations in the proposed binding sites of the AHAS enzyme have in fact exhibited specific resistance to a single class of herbicides (Ott et al. (1996) *J. Mol. Biol.* 263:359-368).

Plant resistance to imidazolinone herbicides has also been reported in a number of patents. U.S. Pat. Nos. 4,761,373, 5,331,107, 5,304,732, 6,211,438, 6,211,439 and 6,222,100 generally describe the use of an altered AHAS gene to elicit herbicide resistance in plants, and specifically discloses certain imidazolinone-resistant corn lines. U.S. Pat. No. 5,013, 659 discloses plants exhibiting herbicide resistance due to mutations in at least one amino acid in one or more conserved regions. The mutations described therein encode either cross-resistance for imidazolinones and sulfonylureas or sulfonylurea-specific resistance, but imidazolinone-specific resistance is not described. U.S. Pat. No. 5,731,180 and U.S. Pat. No. 5,767,361 discuss an isolated gene having a single amino acid substitution in a wild-type monocot AHAS amino acid sequence that results in imidazolinone-specific resistance. In addition, rice plants that are resistant to herbicides that interfere with AHAS have been developed by mutation breeding and also by the selection of herbicide-resistant plants from a pool of rice plants produced by anther culture. See, U.S. Pat. Nos. 5,545,822, 5,736,629, 5,773,703, 5,773,704, 5,952,553 and 6,274,796.

In plants, as in all other organisms examined, the AHAS enzyme is comprised of two subunits: a large subunit (catalytic role) and a small subunit (regulatory role) (Duggleby and Pang (2000) *J. Biochem. Mol. Biol.* 33:1-36). The AHAS large subunit (also referred to herein as AHASL) may be encoded by a single gene as in the case of *Arabidopsis*, rice, and sugar beet or by multiple gene family members as in maize, canola, and cotton. Specific, single-nucleotide substitutions in the large subunit confer upon the enzyme a degree of insensitivity to one or more classes of herbicides (Chang and Duggleby (1998) *Biochem J.* 333:765-777).

For example, bread wheat, *Triticum aestivum* L., contains three homoeologous acetohydroxyacid synthase large subunit genes. Each of the genes exhibit significant expression based on herbicide response and biochemical data from mutants in each of the three genes (Ascenzi et al. (2003) International Society of Plant Molecular Biologists Congress, Barcelona, Spain, Ref. No. S10-17). The coding sequences of all three genes share extensive homology at the nucleotide level (WO 03/014357). Through sequencing the AHASL genes from several varieties of *Triticum aestivum*, the molecular basis of herbicide tolerance in most IMI-tolerant (imidazolinone-tolerant) lines was found to be the mutation S653(At)N, indicating a serine to asparagine substitution at a position equivalent to the serine at amino acid 653 in *Arabidopsis thaliana* (WO 03/01436; WO 03/014357). This mutation is due to a single nucleotide polymorphism (SNP) in the DNA sequence encoding the AHASL protein.

Multiple AHASL genes are also know to occur in dicotyledonous plants species. Recently, Kolkman et al. ((2004) *Theor. Appl. Genet.* 109: 1147-1159) reported the identification, cloning, and sequencing for three AHASL genes (AHASL1, AHASL2, and AHASL3) from herbicide-resistant and wild type genotypes of sunflower (*Helianthus annuus* L.). Kolkman et al. reported that the herbicide-resistance was due either to the Pro197Leu (using the *Arabidopsis* AHASL amino acid position nomenclature) substitution or the Ala205Val substitution in the AHASL1 protein and that each of these substitutions provided resistance to both imidazolinone and sulfonylurea herbicides.

Given their high effectiveness and low-toxicity, imidazolinone herbicides are favored for agricultural use. However, the ability to use imidazolinone herbicides in a particular crop production system depends upon the availability of imidazolinone-resistant varieties of the crop plant of interest. To produce such imidazolinone-resistant varieties, plant breeders need to develop breeding lines with the imidazolinone-resistance trait. Thus, additional imidazolinone-resistant breeding lines and varieties of crop plants, as well as methods and compositions for the production and use of imidazolinone-resistant breeding lines and varieties, are needed.

SUMMARY OF THE INVENTION

The present invention provides sunflower plants having increased resistance to at least one herbicide when compared to a wild-type sunflower plant. In particular, the sunflower plants of the invention have increased resistance to at least one imidazolinone herbicide, particularly imazamox and/or imazapyr, when compared to a wild-type sunflower plant. Unlike previously described imidazolinone-resistant sunflower plants, the sunflower plants of the present invention comprise a novel herbicide-resistance mechanism that does not involve a mutation in gene encoding an acetohydroxyacid synthase large subunit (AHASL) protein. The sunflower plants of the invention also include seeds and progeny plants that comprise at least one copy of a gene or polynucleotide encoding a herbicide-resistant AHASL protein of the invention.

In one embodiment, the present invention provides herbicide-resistant sunflower plants that are from the sunflower line that has been designated herein as MUT31. A sample of seeds of the MUT31 line has been deposited with the American Type Culture Collection (ATCC) as ATCC Patent Deposit No. PTA-7839. The present invention further provides seeds, progeny plants and other descendent plants that comprise the herbicide-resistance characteristics of MUT31.

The present invention provides methods for controlling weeds in the vicinity of the herbicide-resistant sunflower plants of the invention. The methods comprises applying an effective amount of an herbicide to the weeds and to the herbicide-resistant sunflower plant, wherein the herbicide-resistant sunflower plant has increased resistance to at least one herbicide, particularly an imidazolinone herbicide, more particularly imazamoz, when compared to a wild-type sunflower plant. The herbicide can be, for example, applied to the foliage of the plants, to the seeds of the plants prior to planting, and/or to the soil before or after planting.

The present invention further provides methods for producing a herbicide-resistant sunflower plant. The methods involve crossing a first sunflower plant comprising resistance to a herbicide to a second sunflower plant that is not resistant to the herbicide, wherein the first sunflower plant comprises the herbicide-resistance characteristics of MUT31, particularly a MUT31 sunflower plant or any herbicide-resistant descendent of MUT31. Such a herbicide resistant thereof comprises the herbicide-resistance characteristics of MUT31, representative seeds of MUT 31 having been deposited with the ATCC as Patent Deposit Number PTA-7839. The methods further involve selecting for a progeny plant that is resistant to the herbicide.

Additionally, the present invention provides methods for increasing the herbicide-resistance of a sunflower plant. The methods involve crossing a first sunflower plant comprising resistance to a herbicide to a second sunflower plant, wherein the first sunflower plant comprises the herbicide-resistance characteristics of MUT31, particularly a MUT31 sunflower plant or any herbicide-resistant descendent of MUT31. The second sunflower plant can, but is not required to, comprise resistance to at least one herbicide. The methods further involve selecting for a progeny plant that comprises increased herbicide resistance when compared to the herbicide resistance of the second sunflower plant. In one embodiment of the invention, the second sunflower plant comprises at least one herbicide-resistant AHASL gene. Such a second sunflower plant comprises enhanced resistance one or more AHAS-inhibiting herbicides, particularly an imidazolinone herbicide.

BRIEF DESCRIPTION THE DRAWINGS

FIG. 1 is a graphical representation of the results of a 2×3×2 factorial experiment to the test the effects of sunflower genotype (RHA266 or MUT31), herbicide dose (0, 0.25X, and, 0.50X; where X=50 g a.i./ha imazamox), and malathion (0 or 1000 g a.i./ha). The sunflower plants were at the 3-4 leaf growth stage at time of malathion and herbicide spraying. Malathion was sprayed on the plants 30 minutes prior to the imazamox spraying. The sunflower plants were evaluated at 7 days after herbicide spraying to determine damage scores. Additional details are provided below in Example 3.

DETAILED DESCRIPTION OF THE INVENTION

The present invention relates to sunflower plants having increased resistance to at least one herbicide when compared to wild-type sunflower plants. Herbicide-resistant sunflower plants were produced as described hereinbelow by exposing wild-type (with respect to herbicide resistance) sunflower plants to a mutagen, allowing the plants to mature and reproduce, and selecting progeny plants that displayed enhanced resistance to the imidazolinone herbicide, imazamox, when compared to the resistance of a wild-type sunflower plant to the imidazolinone herbicide. The invention provides the novel herbicide-resistant sunflower line that is designated herein as MUT31. While the present invention is not bound by any particular biological mechanism, the herbicide-resistant sunflower plants of invention comprise a novel herbicide-resistance mechanism that is independent of a mutation or mutations in one or more AHASL genes. Thus, the present invention provides a new source of imidazolinone resistance that finds use in methods for controlling weeds and also methods for producing herbicide-resistant sunflower plants or increasing the herbicide resistance of sunflower plants that already comprise herbicide resistance including, but not limited to, imidazolinone-resistance.

For the present invention, the terms "herbicide-tolerant" and "herbicide-resistant" are used interchangeable and are intended to have an equivalent meaning and an equivalent scope. Similarly, the terms "herbicide-tolerance" and "herbicide-resistance" are used interchangeable and are intended to have an equivalent meaning and an equivalent scope. Likewise, the terms "imidazolinone-resistant" and "imidazolinone-resistance" are used interchangeable and are intended to be of an equivalent meaning and an equivalent scope as the terms "imidazolinone-tolerant" and "imidazolinone-tolerance", respectively.

The present invention involves herbicide-tolerant or herbicide-resistant plants and methods for making and using such plants. A "herbicide-tolerant" or a "herbicide-resistant" plant is a plant that is tolerant or resistant to at least one herbicide at a level that would normally kill, or inhibit the growth of, a normal or wild-type plant.

In one embodiment of the invention, the methods of the present invention for increasing the herbicide resistance of a plant involve the use of sunflower plants comprising herbicide-resistant AHASL polynucleotides and herbicide-resistant AHASL proteins. A "herbicide-resistant AHASL polynucleotide" is a polynucleotide that encodes a herbicide-resistant AHASL protein, wherein the protein comprises herbicide-resistant AHAS activity. A "herbicide-resistant AHASL protein" is an AHASL protein that displays higher AHAS activity, relative to the AHAS activity of a wild-type AHASL protein, when in the presence of at least one herbicide that is known to interfere with AHAS activity and at a concentration or level of the herbicide that is to known to inhibit the AHAS activity of the wild-type AHASL protein. Furthermore, the AHAS activity of such a herbicide-tolerant or herbicide-resistant AHASL protein may be referred to herein as "herbicide-tolerant" or "herbicide-resistant" AHAS activity.

Furthermore, it is recognized that a herbicide-tolerant or herbicide-resistant AHASL protein can be introduced into a plant by transforming a plant or ancestor thereof with a nucleotide sequence encoding a herbicide-tolerant or herbicide-resistant AHASL protein. Such herbicide-tolerant or herbicide-resistant AHASL proteins are encoded by the herbicide-tolerant or herbicide-resistant AHASL polynucleotides. Alternatively, a herbicide-tolerant or herbicide-resistant AHASL protein may occur in a plant as a result of a naturally occurring or induced mutation in an endogenous AHASL gene in the genome of a plant or progenitor thereof. Nucleotide sequences encoding herbicide-resistant AHASL proteins and herbicide-resistant plants comprising an endogenous gene that encodes a herbicide-resistant AHASL protein are known in the art. See, for example, U.S. Pat. Nos. 5,013, 659, 5,731,180, 5,767,361, 5,545,822, 5,736,629, 5,773,703, 5,773,704, 5,952,553 and 6,274,796; all of which are herein incorporated by reference.

The present invention provides plants, plant tissues, and plant cells with increased resistance or tolerance to at least one herbicide, particularly an imidazolinone herbicide, more particularly imazamox, imazapyr, or both imazamox and imazapyr. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, or plant cell, but that said amount does not kill or inhibit as severely the growth of the herbicide-resistant plants, plant tissues, and plant cells of the present invention. Typically, the effective amount of a herbicide is an amount that is routinely used in agricultural production systems to kill weeds of interest. Such an amount is known to those of ordinary skill in the art, or can be easily determined using methods known in the art.

The methods of the present invention find use in increasing the herbicide resistance of a sunflower plant, including a sunflower plant that comprises resistance to one or more herbicides, such as, for example, those herbicides that inhibit or otherwise interfere or with the activity of the wild-type AHAS enzyme. Such herbicides may also be referred to herein as "AHAS-inhibiting herbicides" or simply "AHAS inhibitors." As used herein, an "AHAS-inhibiting herbicide" or an "AHAS inhibitor" is not meant to be limited to single herbicide that interferes with the activity of the AHAS enzyme. Thus, unless otherwise stated or evident from the context, an "AHAS-inhibiting herbicide" or an "AHAS inhibitor" can be one herbicide or a mixture of two, three, four, or more herbicides, each of which interferes with the activity of the AHAS enzyme.

By "wild-type, sunflower plant, plant tissue, or plant cell" is intended a sunflower plant, plant tissue, or plant cell, respectively, that lacks the herbicide-resistance characteristics of the herbicide-resistant sunflower plants of the present invention, particularly MUT31 and herbicide-resistant descendents thereof. The use of the term "wild-type" is not, therefore, intended to imply that a sunflower plant, plant tissue, or plant cell lacks recombinant DNA in its genome, and/or lacks herbicide-resistant characteristics that are different from those disclosed herein.

As used herein unless clearly indicated otherwise, the term "plant" intended to mean a plant at any developmental stage, as well as any part or parts of a plant that may be attached to or separate from a whole intact plant. Such parts of a plant include, but are not limited to, organs, tissues, and cells of a plant. Examples of particular plant parts include a stem, a leaf, a root, an inflorescence, a flower, a floret, a fruit, a pedicle, a peduncle, a stamen, an anther, pollen, a stigma, a style, an ovary, a petal, a sepal, a carpel, a root tip, a root cap, a root hair, a leaf hair, a seed hair, a pollen grain, a microspore, a cotyledon, a hypocotyl, an epicotyl, xylem, phloem, parenchyma, endosperm, a companion cell, a guard cell, and any other known organs, tissues, and cells of a plant. Furthermore, it is recognized that a seed is a plant.

The sunflower plants of the present invention include both non-transgenic plants and transgenic plants. By "non-transgenic plant" is intended to mean a plant lacking recombinant DNA in its genome. By "transgenic plant" is intended to mean a plant comprising recombinant DNA in its genome. Such a transgenic plant can be produced by introducing recombinant DNA into the genome of the plant. When such recombinant DNA is incorporated into the genome of the transgenic plant, progeny of the plant can also comprise the recombinant DNA. A progeny plant that comprises at least a portion of the recombinant DNA of at least one progenitor transgenic plant is also a transgenic plant.

The present invention provides the herbicide-resistant sunflower line that is referred to herein as MUT31. A deposit of at least 2500 seeds from sunflower (*Helianthus annuus* L.) line MUT31 was made under the Budapest Treaty with the Patent Depository of the American Type Culture Collection (ATCC), Manassas, Va. 20110 USA on Aug. 22, 2006 and assigned ATCC Patent Deposit Number PTA-7839. The deposit of sunflower line MUT31 was made for a term of at least 30 years and at least 5 years after the most recent request for the furnishing of a sample of the deposit is received by the ATCC. The deposit will be maintained under the terms of the Budapest Treaty on the International Recognition of the Deposit of Microorganisms for the Purposes of Patent Procedure. The deposit of sunflower line MUT31 was made for a term of at least 30 years and at least 5 years after the most recent request for the furnishing of a sample of the deposit is received by the ATCC. Additionally, Applicants have satisfied all the requirements of 37 C.F.R. §§1.801-1.809, including providing an indication of the viability of the sample. Applicants impose no restrictions on the availability of the deposited material from the ATCC after the issuance of a patent from this application. However, Applicants have no authority to wave any restrictions imposed by law on the transfer of biological material or its transportation in commerce. Applicants do not waive any infringement of Applicants' rights granted under such patent.

The present invention provides herbicide-resistant sunflower plants of the MUT31 line that were produced by a mutation breeding. Wild-type sunflower plants were mutagenized by exposing the plants to a mutagen, particularly a chemical mutagen, more particularly ethyl methanesulfonate (EMS). However, the present invention is not limited to herbicide-resistant sunflower plants that are produced by a mutagenesis method involving the chemical mutagen EMS. Any mutagenesis method known in the art may be used to produce the herbicide-resistant sunflower plants of the present invention. Such mutagenesis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radioisotopes such as phosphorus 32 or carbon 14), and ultraviolet radiation (preferably from 2500 to 2900 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by reference.

Sunflower plants and seeds of the present invention comprise the herbicide resistance characteristics of MUT31. Such plants and seeds may be referred to herein as comprising the MUT31 trait. The MUT31 trait confers resistance to imidazolinone herbicides to a plant or seed possessing this trait whether the trait is in the heterozygous or homozygous state in the plant. In particular, the MUT31 trait confers to a sunflower plant or seed resistance to at least one imidazolinone herbicide, particularly imazamox and/or imazapyr, wherein the imidazolinone resistance is reduced or inhibited by the organophosphate insecticide malathion. As described hereinbelow, the resistance or tolerance of MUT31 sunflower plants to the imidazolinone herbicide imazamox was found to be reduced or inhibited following the application of malathion to the MUT31 sunflower plants prior to the application of imazamox. Thus, sunflower plants and seeds comprising the MUT31 trait comprise malathion-inhibitable, imidazolinone resistance. While the present invention is not bound to a particular biological mechanism, the herbicide resistance of MUT31 sunflower plants or the MUT31 trait is believed to be due to an induced mutation in a single gene within the sunflower nuclear genome.

The sunflower plants of the present invention include, for example, descendents of the MUT31 line that are heterozygous or homozymgous for the MUT31 trait. It is recognized that such descendents can be produced via sexual reproduction or by any asexual reproduction methods known in the art such as for example, tissue culture. Descendents of the MUT31 line that comprise the MUT31 trait can be identified by determining if a descendent sunflower plant comprises malathion-inhibitable, imidazolinone resistance. The present invention does not depend on a particular method for determining if a descendent sunflower plant comprises malathion-inhibitable, imidazolinone resistance. Any method know in the art can be used including the method disclosed in Example 3 below to determine if a descendent of MUT31 comprises malathion-inhibitable, imidazolinone resistance. The method involves applying malathion to a descendent of MUT31 prior to the application of the imidazolinone herbicide and determining whether malathion reduces or inhibits the resistance of the descendent to the imidazolinone herbicide. Descendents that comprise the MUT31 trait comprise malathion-inhibitable, imidazolinone resistance. Thus, the sunflower plants of the present invention include, for example, those sunflower plants that are descendents of MUT31 and comprise malathion-inhibitable, imidazolinone resistance.

The present invention provides methods for enhancing the tolerance or resistance of a sunflower plant, plant tissue, plant cell, or other host cell to at least one herbicide, particularly an imidazolinone herbicide or mixture two or more imidazolinone herbicides. For the present invention, the imidazolinone herbicides include, but are not limited to, PURSUIT ® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, and a mixture of two or more of the aforementioned herbicides, for example, imazapyr/imazamox (ODYSSEY®). More specifically, the imidazolinone herbicide can be selected from, but is not limited to, 2-(4-isopropyl-4-methyl-5-oxo-2-imidiazolin-2-yl)-nicotinic acid, 2-(4-isopropyl)-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, and a mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate. The use of 5-ethyl-2-(4-isopropyl-4-methyl-5-oxo-2-imidazo lin-2-yl)-nicotinic acid and 2-(4-isopropyl-4-methyl-5-oxo-2-imidazolin-2-yl)-5-(methoxymethyl)-nicotinic acid is preferred. The use of 2-(4-isopropyl-4-methyl-5-oxo-2-imidazolin-2-yl)-5-(methoxymethyl)-nicotinic acid is particularly preferred.

The herbicide-resistant plants of the invention find use in methods for controlling weeds. Thus, the present invention further provides a method for controlling weeds in the vicinity of a herbicide-resistant sunflower plant of the invention. The method comprises applying an effective amount of a herbicide to the weeds and to the herbicide-resistant sunflower plant, wherein the plant has increased resistance to at least one herbicide, particularly an imidazolinone or sulfonylurea herbicide, when compared to a wild-type plant. In such a method for controlling weeds, the herbicide-resistant plants of the invention are preferably crop plants, including, but not limited to, sunflower, alfalfa, Brassica sp., soybean, cotton, safflower, peanut, tobacco, tomato, potato, wheat, rice, maize, sorghum, barley, rye, millet, and sorghum.

By providing plants having increased resistance to herbicides, particularly imidazolinone and sulfonylurea herbicides, a wide variety of formulations can be employed for protecting plants from weeds, so as to enhance plant growth and reduce competition for nutrients. A herbicide can be used by itself for pre-emergence, post-emergence, pre-planting and at planting control of weeds in areas surrounding the plants described herein or an imidazolinone herbicide formulation can be used that contains other additives. The herbicide can also be used as a seed treatment. That is an effective concentration or an effective amount of the herbicide, or a composition comprising an effective concentration or an effective amount of the herbicide can be applied directly to the seeds prior to or during the sowing of the seeds. Additives found in an imidazolinone or sulfonylurea herbicide formulation or composition include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. The herbicide and herbicide formulations can be applied in accordance with conventional methods, for example, by spraying, irrigation, dusting, coating, and the like.

The present invention provides seeds with increased resistance to at least one herbicide, particularly an imidazolinone herbicide. Such seeds include, for example, sunflower seeds that are herbicide-resistant descendents of the MUT31 sunflower line.

A "descendent" of the MUT31 sunflower line comprises any plant, plant cell, or plant part that is derived by sexual and/or asexual propagation from MUT31, representative seeds of MUT31 having been deposited with the ATCC and assigned ATCC Patent Deposit No. PTA-7839. For example, such a descendent includes a plant produced by crossing a first plant with a second plant to produce a seed of the third plant (i.e., a descendent), wherein the first plant is a MUT31 sunflower plant and the second is another sunflower plant that is not a MUT31 sunflower plant. Such a descendent also includes any plants that are descended from the third plant whether produced by sexual and/or asexual propagation. For example, cells, tissue or an organ from the third plant could be used to produce a fourth plant by an asexual propagation method including, but not limited to, in vitro plant cell, tissue, and organ culture methods and methods involving the rooting of stem cuttings.

For the present invention, a herbicide-resistant descendent of MUT31 is a descendent of MUT31 that comprises the herbicide-resistance characteristics of MUT31 by way of being descended from one or more MUT31 sunflower plants. In other words, such a herbicide-resistant descendent has inherited the herbicide-resistance characteristics of a MUT31 sunflower plant by sexual reproduction, asexual reproduction, or combination thereof.

Unless otherwise clearly indicated or apparent from the context, the "progeny" of a plant includes a plant of any subsequent generation whose ancestry can be traced to that plant. Similar, unless otherwise clearly indicated by context, the "herbicide resistant progeny" of MUT31 includes a plant of any subsequent generation whose ancestry can be traced to MUT31 and that comprises the herbicide-resistance characteristics of MUT31 by way of that ancestry.

The present invention provides methods for producing a herbicide-resistant sunflower plant, particularly a herbicide-resistant sunflower plant, through conventional plant breeding involving sexual reproduction. The methods comprise crossing a first plant comprises resistance to a herbicide to a second plant that is not resistant to the herbicide. The first plant can be any of the herbicide-resistant plants of the present invention including, for example, sunflower plants that comprise the herbicide-resistance characteristics of the MUT31 sunflower plant, particularly MUT31 sunflower plants and herbicide-resistant descendents of MUT31. The second plant can be any plant that is capable of producing viable progeny plants (i.e., seeds) when crossed with the first plant. Typically, but not necessarily, the first and second plants arc of the same species. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The methods of the invention can additionally involve selecting plants that comprise the herbicide-resistance characteristics of the first plant.

The present invention further provides methods for increasing the herbicide-resistance of a plant, particularly a herbicide-resistant sunflower plant, through conventional plant breeding involving sexual reproduction. The methods comprise crossing a first plant comprises resistance to a herbicide to a second plant that may or may not be resistant to the herbicide or may be resistant to a different herbicide or herbicides than the first plant. The first plant can be any of the herbicide-resistant sunflower plants of the present invention including, for example, a MUT31 sunflower plants and a herbicide-resistant descendent thereof. The second plant can be any plant that is capable of producing viable progeny plants (i.e., seeds) when crossed with the first plant. Typically, but not necessarily, the first and second plants are of the same species. The progeny plants produced by this method of the present invention have increased or enhanced resistance to a herbicide when compared to either the first or second plant or both. When the first and second plants are resistant to different herbicides, the progeny plants will have the combined herbicide-resistance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The methods of the invention can additionally involve selecting plants that comprise the herbicide-resistance characteristics of the first plant, the second plant, or both the first and the second plant.

The present invention provides methods for enhancing or increasing the resistance of a sunflower plant to at least one imidazolinone herbicide. Imidazolinone herbicides are known as AHAS-inhibiting herbicides because of their recognized ability to inhibit AHAS activity in vivo and in vitro. In addition to imidazolinone herbicides, AHAS-inhibiting herbicides include, for example, sulfonylurea herbicides, triazolopyrimidine herbicides, pyrimidinyloxybenzoate herbicides, and sulfonylamino-carbonyltriazolinone herbicides.

In an embodiment of the invention, the methods involve enhancing or increasing the resistance of a herbicide-resistant sunflower plant that comprises resistance to an AHAS-inhibiting herbicide, wherein the resistance to the AHAS-inhibiting herbicide is due to one or more herbicide-resistant AHASL proteins. Such a herbicide-resistant sunflower plant can be resistant to one or more AHAS-inhibiting herbicides such as, for example, an imidazolinone herbicide, a sulfonylurea herbicide, a triazolopyrimidine herbicide, a pyrimidinyloxybenzoate herbicide, a sulfonylamino-carbonyltriazolinone herbicide, or mixture thereof. Examples of some suitable imidazolinone herbicides are described above. Sulfonylurea herbicides include, but are not limited to, chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, flazasulfuron, imazosulfuron, pyrazosulfuron ethyl, halosulfuron, azimsulfuron, cyclosulfuron, ethoxysulfuron, flazasulfuron, flupyrsulfuron methyl, foramsulfuron, iodosulfuron, oxasulfuron, mesosulfuron, prosulfuron, sulfosulfuron, trifloxysulfuron, tritosulfuron, a derivative of any of the aforementioned herbicides, and a mixture of two or more of the aforementioned herbicides. The triazolopyrimidine herbicides of the invention include, but, are not limited to, cloransulam, diclosulam, florasulam, flumetsulam, metosulam, and penoxsulam. The pyrimidinyloxybenzoate herbicides of the invention include, but are not limited to, bispyribac, pyrithiobac, pyriminobac, pyribenzoxim and pyriftalid. The sulfonylamino-carbonyltriazolinone herbicides include, but are not limited to, flucarbazone and propoxycarbazone.

It is recognized that pyrimidinyloxybenzoate herbicides are closely related to the pyrimidinylthiobenzoate herbicides and are generalized under the heading of the latter name by the Weed Science Society of America. Accordingly, the herbicides of the present invention further include pyrimidinylthiobenzoate herbicides, including, but not limited to, the pyrimidinyloxybenzoate herbicides described above.

The sunflower plants of the present invention can be non-transgenic or transgenic. Examples of non-transgenic sunflower plants having increased resistance to at least one imidazolinone herbicide include the MUT31 sunflower plant, representative seeds of MUT31 having been deposited with the ATCC as Patent Deposit No. PTA-7839; or mutant, recombinant, or a genetically engineered derivative of MUT31; or of any progeny of MUT31; or a plant that is a progeny of any of these plants; or a plant that comprises the herbicide-resistance characteristics of MUT31, particularly a herbicide-resistant descendent of MUT31. An example of a transgenic sunflower plant having increased resistance to at least one imidazolinone herbicide is a sunflower plant that is a genetically engineered derivative of MUT31 that comprises the herbicide-resistance characteristics of MUT31. Such a genetically engineered derivative can comprises in its genome, for example, a transgene of interest including, but not limited to, a herbicide-resistant AHASL gene, a gene conferreing disease resistance, and a gene conferreing insect resistance.

The present invention provides methods that involve the use of an imidazolinone herbicide. In these methods, the imidazolinone herbicide can be applied by any method known in the art including, but not limited to, seed treatment, soil treatment, and foliar treatment.

Prior to application, the imidazolinone herbicide can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

Examples of suitable carriers are ground natural minerals (for example kaolins, clays, talc, chalk) and ground synthetic minerals (for example highly disperse silica, silicates).

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example Dichlorophen and enzylalkoholhemiformal.

Seed Treatment formulations may additionally comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethanes, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An examples of a suitable gelling agent is carrageen (Satiagel®)

Powders, materials for spreading, and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the imidazolinone herbicide. In this case, the imidazolinone herbicides are employed in a purity of from 90% to 100% by weight, preferably 95% to 100% by weight (according to NMR spectrum). For seed treatment purposes, respective formulations can be diluted 2-10 fold leading to concentrations in the ready to use preparations of 0.01 to 60% by weight active compound by weight, preferably 0.1 to 40% by weight.

The imidazolinone herbicide can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the imidazolinone herbicide according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The imidazolinone herbicide may also be used successfully in the ultra-low-volume process (ULV), it being possible to apply formulations comprising over 95% by weight of active compound, or even to apply the active compound without additives.

The following are examples of formulations:
1. Products for dilution with water for foliar applications. For seed treatment purposes, such products may be applied to the seed diluted or undiluted.
   A) Water-soluble concentrates (SL, LS)
      Ten parts by weight of the imidazolinone herbicide are dissolved in 90 parts by weight of water or a water-soluble solvent. As an alternative, wetters or other auxiliaries are added. The imidazolinone herbicide dissolves upon dilution with water, whereby a formulation with 10% (w/w) of imidazolinone herbicide is obtained.

B) Dispersible concentrates (DC)

Twenty parts by weight of the imidazolinone herbicide are dissolved in 70 parts by weight of cyclohexanone with addition of 10 parts by weight of a dispersant, for example polyvinylpyrrolidone. Dilution with water gives a dispersion, whereby a formulation with 20% (w/w) of imidazolinone herbicide is obtained.

C) Emulsifiable concentrates (EC)

Fifteen parts by weight of the imidazolinone herbicide are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of imidazolinone herbicide is obtained.

D) Emulsions (EW, EO, ES)

Twenty-five parts by weight of the imidazolinone herbicide are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of imidazolinone herbicide is obtained.

E) Suspensions (SC, OD, FS)

In an agitated ball mill, 20 parts by weight of the imidazolinone herbicide are comminuted with addition of 10 parts by weight of dispersants, wetters and 70 parts by weight of water or of an organic solvent to give a fine imidazolinone herbicide suspension. Dilution with water gives a stable suspension of the imidazolinone herbicide, whereby a formulation with 20% (w/w) of imidazolinone herbicide is obtained.

F) Water-dispersible granules and water-soluble granules (WG, SG)

Fifty parts by weight of the imidazolinone herbicide are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the imidazolinone herbicide, whereby a formulation with 50% (w/w) of imidazolinone herbicide is obtained.

G) Water-dispersible powders and water-soluble powders (WP, SP, SS, WS)

Seventy-Five Parts by Weight of the Imidazolinone Herbicide are ground in a rotor-stator mill with addition of 25 parts by weight of dispersants, welters and silica gel. Dilution with water gives a stable dispersion or solution of the imidazolinone herbicide, whereby a formulation with 75% (w/w) of imidazolinone herbicide is obtained.

I) Gel-Formulation (GF)

In an agitated ball mill, 20 parts by weight of the imidazolinone herbicide are comminuted with addition of 10 parts by weight of dispersants, 1 part by weight of a gelling agent wetter and 70 parts by weight of water or of an organic solvent to give a fine imidazolinone herbicide suspension. Dilution with water gives a stable suspension of the imidazolinone herbicide, whereby a formulation with 20% (w/w) of imidazolinone herbicide is obtained. This gel formulation is suitable for us as a seed treatment.

2. Products to be applied undiluted for foliar applications. For seed treatment purposes, such products may be applied to the seed diluted.

A) Dustable powders (DP, DS)

Five parts by weight of the imidazolinone herbicide are ground finely and mixed intimately with 95 parts by weight of finely divided kaolin. This gives a dustable product having 5% (w/w) of imidazolinone herbicide.

B) Granules (GR, FG, GG, MG)

One-half part by weight of the imidazolinone herbicide is ground finely and associated with 95.5 parts by weight of carriers, whereby a formulation with 0.5% (w/w) of imidazolinone herbicide is obtained. Current methods are extrusion, spray-drying or the fluidized bed. This gives granules to be applied undiluted for foliar use.

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds.

In a preferred embodiment a FS formulation is used for seed treatment. Typcially, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

The present invention provides seeds of the herbicide-resistant plants of the present invention, particularly seeds that are herbicide-resistant descendents of MUT31. For seed treatment, seeds of the present invention are treated with herbicides, preferably herbicides selected from the group consisting of AHAS-inhibiting herbicides such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, and mixtures thereof, or with a formulation comprising a AHAS-inhibiting herbicide. Preferably, the AHAS-inhibiting herbicides of the present invention are imidazolinone herbicides.

The term seed treatment comprises all suitable seed treatment techniques known in the art, such as seed dressing, seed coating, seed dusting, seed soaking, and seed pelleting.

In accordance with one variant of the present invention, a further subject of the invention is a method of treating soil by the application, in particular into the seed drill: either of a granular formulation containing the imidazolinone herbicide as a composition/formulation (e.g. a granular formulation, with optionally one or more solid or liquid, agriculturally acceptable carriers and/or optionally with one or more agriculturally acceptable surfactants. This method is advantageously employed, for example, in seedbeds of cereals, maize, cotton, and sunflower.

The present invention also comprises seeds coated with or containing with a seed treatment formulation comprising at least one ALS inhibitor selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

The seed treatment application with the imidazolinone herbicide or with a formulation comprising the imidazolinone herbicide is carried out by spraying or dusting the seeds before sowing of the plants and before emergence of the plants.

In the treatment of seeds, the corresponding formulations are applied by treating the seeds with an effective amount of the imidazolinone herbicide or a formulation comprising the imidazolinone herbicide. Herein, the application rates are generally from 0.1 g to 10 kg of the a.i. (or of the mixture of a.i. or of the formulation) per 100 kg of seed, preferably from 1 g to 5 kg per 100 kg of seed, in particular from 1 g to 2.5 kg per 100 kg of seed. For specific crops such as lettuce the rate can be higher.

The present invention provides a method for combating undesired vegetation or controlling weeds comprising contacting the seeds of the resistant plants according to the present invention before sowing and/or after pregermination with an imidazolinone herbicide. The method can further comprise sowing the seeds, for example, in soil in a field or in a potting medium in greenhouse. The method finds particular use in combating undesired vegetation or controlling weeds in the immediate vicinity of the seed.

The control of undesired vegetation is understood as meaning the killing of weeds and/or otherwise retarding or inhibiting the normal growth of the weeds. Weeds, in the broadest sense, are understood as meaning all those plants which grow in locations where they are undesired.

The weeds of the present invention include, for example, dicotyledonous and monocotyledonous weeds. Dicotyledonous weeds include, but are not limited to, weeds of the genera: Sinapis, *Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*.

In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation.

Example 1

Mutagenesis of *Helianthus annuus* Line RHA266 and Selection of Imidazolinone-Resistant Plants In the spring of the first growing season, forty rows of sunflower (*Helianthus annuus*) line RHA266 were sown outdoors at the Advanta Semillas Biotech Research Station in Balcarce, BsAs, Argentina and then a portion of the plants were treated with ethyl methanesulfonate (EMS, also referred to as methanesulfonic acid ethyl ester). EMS is a known mutagen that typically induces G•C-to-A•T transitions in DNA (Jander et al. (2003) *Plant Physiol.* 131:139-146). Plants were treated with a solution comprising 0.5%, 5%, or 10%, (w/v) EMS. For each EMS treatment, 13 rows of sunflower plants were treated. Before flowering, all $M_0$ plants were bagged in order to ensure that the resulting $M_1$ seeds were the product of self-pollination. The seed heads from each EMS treatment were harvested and threshed in bulk. In the following growing season, the $M_1$ seeds were sown outdoors with each treatment in a separate plot. Twenty days later, when the plants were at the 2-4 leaf pair growth stage, all of the EMS-treated plants were sprayed with 2X of SWEEPER 70DG (100 g a.i./ha). The active ingredient in SWEEPER is imazamox. After the herbicide spraying, a total of 54 plants survived and were selected as putative resistant. Forty-four resistant plants reached flowering, produced pollen, and $M_2$ seed. The distribution of the forty-four fertile resistant plants per EMS treatment is indicated in Table 1.

TABLE 1

Number of $M_1$ Imidazolinone-Resistant Sunflower Plants Recovered from Each EMS Treatment

| EMS Concentration (%) | No. of Resistant Plants Recovered |
|---|---|
| 0.5 | 19 |
| 5.0 | 9 |
| 10 | 16 |

Tissue samples were taken from each individual surviving $M_1$ plant and DNA from each sample was extracted for PCR amplification and sequencing studies described below in Example 2.

M$_2$ seeds that were produced by each of the forty-four fertile M$_1$ plants were sown in individual plots in Fargo, N.D. then sprayed with 0.5X of SWEEPER 70DG (25 g ai/ha imazamox) at the 2-4 leaf pair growth stage. One of the plots was selected as homozygous tolerant and designated as MUT31. Nineteen M$_2$ plants of MUT31 were harvested, their M$_{2.3}$ progenies sown in Balcarce in the summer of 2003-2004, and the resulting plants allowed to mature and then selfed. M$_4$ seed from one plot was harvested and declared breeder seed on the basis of phenotypic observations. (Breeder seed is seed produced by the direct control of the plant breeder and is the basis of the first and recurring increase of foundation seeds.)

Example 2

PCR Amplification and Sequencing of Sunflower Polynucleotides Encoding Imidazolinone-Resistant and Wild-Type AHASL1 Proteins To attempt to determine the origin of the imidazolinone tolerance in the sunflower plants of Example 1, polymerase chain reaction (PCR) amplification of genomic DNA was employed to amplify the entire coding regions of each to the sunflower AHASL1, AHASL2, and AHASL3 genes. For the PCR amplifications, genomic DNA was isolated from tissue of the M$_1$ MUT31 sunflower plant. Control, wild-type genomic DNA was also isolated from tissue of an RHA266 sunflower plant for PCR amplifications of each of the wild-type AHASL genes. The resulting PCR products were sequenced to determine the DNA sequences of the AHASL1, AHASL2, and AHASL3 genes from the MUT31 and RHA266 plants.

Surprisingly, when the DNA sequences of the AHASL1, AHASL2, and AHASL3 genes from MUT31 were aligned and compared to their corresponding DNA sequences from RHA266, no differences were detected (data not shown). While the present invention is not bound by any particular biological mechanism, these results indicate that the sunflower plants of the MUT31 comprise a novel herbicide-resistance mechanism that is independent of a mutation or mutations in one or more AHASL genes.

Example 3

Analysis of Herbicide Detoxification by MUT31

To evaluate the detoxification ability of MUT31 sunflower plants, an experiment was conducted in the greenhouse. The objective of the experiment was to determine if the imazamox tolerance of MUT31 plants is associated with detoxification mechanism that is mediated by a P450 monooxygenase enzyme (referred to herein as "P450 enzyme"). It was previously reported that the organophosphate insecticide malathion (diethyl-dimethoxythiophosphorylthio-succinate) specifically inhibits P450 enzymes by blocking the herbicide detoxification activity (Yu et al. (2004) *Pest. Biochem. Physiol.* 78:21-30). Thus, plants comprising enhanced herbicide tolerance that is due to an altered P450 enzyme are expected to become less tolerant or susceptible to the herbicide when malthion is applied to the plants before they are treated with the herbicide.

A factorial experiment with three factors: genotypes (MUT31 and RHA266), herbicide dose (Control, 0.25X, and 0.50X; where X=50 g ai/ha imazamox) and malathion (with or without malathion) was arranged in a randomized split-split plot block design. Imazamox (SWEEPER) was sprayed at the 3-4 leaf growth stage. The P450 inhibitor malathion was sprayed at a rate of 1000 g ai/ha 30 minutes prior to herbicide spraying. The evaluation of the plants was carried out seven days after herbicide spraying, using the criteria set forth in Table 2.

TABLE 2

Criteria for Herbicide Damage Scores for Plant Evaluations

| Symptom | Damage score |
|---|---|
| Chlorosis, yellow flash | 5-10% |
| Growth rate reduction, internodes shortening | 10-20% |
| Leaf deformations | 20-30% |
| Necrosis | 30-45% |
| Dead plant | +50% |

The application of malathion in the absence of herbicide had no effect on the response of the MUT31 and RHA266 sunflower lines; both the mean and variance were zero (Table 3). Both lines were more tolerant (lower damage % score) when malathion was not sprayed before imazamox. When the plants were treated with 0.5X imazamox alone, MUT31 showed a significant increase in herbicide tolerance with respect to the control RHA266. The herbicide tolerance of MUT31 significantly decreased (higher score) after malathion treatment (Table 3, FIG. 1). The results of the statistical analysis are presented in Table 4.

The results of this factorial experiment indicate that malathion inhibited the herbicide tolerance exhibited by MUT31 and suggest that the herbicide tolerant phenotype of MUT31 may be due to detoxification mechanism mediated by one or more altered P450 enzymes. Although the present invention does not depend on any particular biological mechanism for enhanced herbicide resistance, these results further suggest that the MUT31 sunflower plant comprises in its genome one or more mutations in one or more genes encoding P450 enzymes.

TABLE 3

Mean Herbicide Damage Score Values

| | Herbicide dose | | | | | |
|---|---|---|---|---|---|---|
| | 0x (control) | | 0.25x | | 0.50x | |
| Malathion | No | Yes | No | Yes | No | Yes |
| MUT31 | 0.00 | 0.00 | 9.50 | 30.35 | 20.13 | 40.31 |
| RHA266 | 0.00 | 0.00 | 27.95 | 45.30 | 42.35 | 45.50 |

TABLE 4

Statistical Analysis of the Factorial Experiment MUT-31 and RHA266

| Source | Df | MeanSq | F | Pr(>F) | Significance |
|---|---|---|---|---|---|
| Replicates | 3 | 38.2 | | | |
| Malathion | 1 | 1893.43 | 122.01 | 0.001589 | ** |
| Error (a) | 3 | 15.52 | | | |
| Herbicide dose | 1 | 619.08 | 34.966 | 0.001041 | ** |
| Malathion × dose | 1 | 110.45 | 6.2381 | 0.046678 | * |
| Error (b) | 6 | 17.71 | | | |
| Line | 1 | 1849.08 | 101.6794 | 3.27E-07 | *** |
| Malathion × Line | 1 | 210.89 | 11.5969 | 0.005217 | ** |
| Dose × Line | 1 | 17.93 | 0.9857 | 0.340397 | |
| Malathion × Dose × Line | 1 | 91.63 | 5.0388 | 0.044418 | * |
| Residuals | 12 | 18.19 | | | |

Example 4

Herbicide Tolerance of Sunflower Lines with MUT31 and a Herbicide-Tolerant AHASL Gene A field trial was conducted to compare the herbicide tolerance of sunflower hybrids carrying the MUT31 trait and the A205V mutation in a sunflower AHASL gene (A205V/A205V). A sunflower AHASL gene with the A205V mutation encodes a AHASL protein which has a valine at amino acid that corresponds to amino acid position 205 in the *Arabidopsis thaliana* AHASL protein. The amino acid at the same position in a wild-type sunflower AHASL protein is alanine. In the amino acid sequence of the sunflower AHASL protein, this alanine-to-valine amino acid substitution is at amino acid position 190. By convention, the sites of amino acid substitutions that are known to give rise to herbicide resistance in plant AHASL proteins are typically referred to by the position of the substitution in the amino acid sequence of the *Arabidopsis* AHASL protein.

TABLE 5

Description of Sunflower Lines Tested

| Entry | Type of Material | Mut event | Zygosity | Entry Description |
|---|---|---|---|---|
| 1 | IMI Restorer | A205V | homo | hybrid |
| 2 | IMI cms × IMI restorer | A205V | homo | hybrid |
| 3 | WT × IMI restorer | A205V | hetero | hybrid |
| 4 | WT × IMI restorer | A205V | hetero | hybrid |
| 5 | A837 cms × IMI restorer | A205V | hetero | hybrid |
| 6 | IMI cms × MUT31 restorer | A205V/MUT31 | hetero | hybrid |
| 7 | WT | — | — | line |
| 8 | MUT31 Restorer | MUT31 | homo | line |

Seed from each entry was produced under optimum seed production conditions in South America in 2005/2006. The field trial was conducted at one location in North Dakota, USA in 2006. The entries were organized in a randomized complete block using a split plot design consisting of 3 replications for each treatment combination. Factor A was the herbicide treatment, and factor B was the sunflower entry. The plot size was 4 rows×12 ft and the seeding rate was consistent with local agronomic practices. The herbicide rates for each treatment for Entries 1-6 are shown in Table 6. The herbicide rates for each treatment for Entries 8 are shown in Table 7. The spray volume was 10 gallons per acre (GPA) (or 100 liters/ha) for a backpack sprayer or 20 GPA (or 200 liters/ha) for a tractor mounted boom. The herbicide treatments were applied at the 2-4 leaf growth stage.

TABLE 6

Factor A, Herbicide Treatment List for Entries 1-6:

| Treatment No. | Treatment |
|---|---|
| 1 | Untreated |
| 2 | 50 g ai/ha imazamox + 0.25% (v/v) NIS |
| 3 | 100 g ai/ha imazamox + 0.25% (v/v) NIS |
| 4 | 200 g ai/ha imazamox + 0.25% (v/v) NIS |
| 5 | 160 g ai/ha imazapyr + 0.25% (v/v) NIS |

NIS = non-ionic surfactant

TABLE 7

Factor A, Herbicide Treatment List for Entry 8:

| Treatment No. | Treatment |
|---|---|
| 1 | Untreated |
| 2 | 12.5 g ai/ha imazamox + 0.25% (v/v) NIS |
| 3 | 25 g ai/ha imazamox + 0.25% (v/v) NIS |
| 4 | 37.5 g ai/ha imazamox + 0.25% (v/v) NIS |
| 5 | 80 g ai/ha imazapyr + 0.25% (v/v) NIS |

NIS = non-ionic surfactant

Entry 7 (WT Maintainer line) was left unsprayed in all treatment blocks. Each herbicide treatment was tested on a WT border plot to ensure efficacy of the product (100% crop injury at 21 days post spray).

Phytotoxicity ratings were assessed at 7 days and 21 days following herbicide application. Phytotoxicity was recorded as the amount of plant damage (in percent), where a rating of '0' indicated no damage to the plants in the plot relative to the untreated plot. A rating of '100' indicated complete necrosis (death) of the plants in the plot relative to the untreated plot.

The data was subjected to an ANOVA analysis and the means from the 3 repetitions are presented in Table 8 (phytotoxicity at 21 days post-treatment).

TABLE 8

Phytotoxicity Ratings (% Crop Injury) recorded 21 Days after Treatment (DAT)

| Entry | Type of Material | Mut event | Zygosity | 21 DAT 50 G IMAZAMOX | 21 DAT 100 G IMAZAMOX | 21 DAT 200 G IMAZAMOX | 21 DAT 160 G IMAZAPYR | 21 DAT UNTREATED |
|---|---|---|---|---|---|---|---|---|
| 1 | IMI Restorer | A205 | homo | 5.00 | 6.67 | 15.00 | 6.67 | 0.00 |
| 2 | IMI cms × IMI restorer | A205 | homo | 0.00 | 3.33 | 21.67 | 3.33 | 0.00 |
| 3 | WT × IMI restorer | A205 | hetero | 6.67 | 25.00 | 73.33 | 20.00 | 0.00 |
| 4 | WT × IMI restorer | A205 | hetero | 11.67 | 46.67 | 76.67 | 43.33 | 0.00 |
| 5 | A837 cms × IMI restorer | A205 | hetero | 3.33 | 40.00 | 78.33 | 36.67 | 0.00 |
| 6 | IMI cms × MUT31 restorer | A205/MUT31 | hetero | 1.67 | 10.00 | 43.33 | 10.00 | 0.00 |
| 7 | WT | | | 0.00 | 0.00 | 0.00 | 0.00 | 0.00 |

| Entry | Type of Material | Mut event | Zygosity | 21 DAT 12.5 G IMAZAMOX | 21 DAT 25 G IMAZAMOX | 21 DAT 37.5 G IMAZAMOX | 21 DAT 80 G IMAZAPYR | 21 DAT UNTREATED |
|---|---|---|---|---|---|---|---|---|
| 8 | MUT31 Restorer | MUT31 | homo | 15.00 | 25.00 | 46.67 | 88.33 | 0.00 |

LSD = 8.89
CV = 56.78
St Dev = 5.55

The phytotoxicity in the heterozygous A205V entries (entries 3-5) was significantly higher than the double heterozygous A205V/MUT31 entry (entry 6) at 21 days after treatment with imazamox and imazapyr. The homozygous A205V entries (entries 1-2) demonstrated the lowest levels of phytotoxicity or crop injury (Table 1). At 100 g ai/ha of imazamox the range in phytotoxicity of the A205V heterozygous entries was between 25% and 47% compared to an injury rating of 10% for the A205V/MUT31 heterozygous entry. At 200 g ai/ha of imazamox the range in phytotoxicity of the A205V heterozygous entries was between 73% and 78% injury compared to an injury rating of 43% for the A205V/MUT31 heterozygous entry. With 160 g ai/ha of imazapyr the range in phytotoxicity of the A205V heterozygous entries was between 20% and 43% injury compared to an injury rating of 10% for the A205V/MUT31 heterozygous entry.

When MUT31 alone (entry 8) was challenged with 37.5 g ai/ha of imazamox, it demonstrated an injury rating of 47% at 21 days after treatment. From previous studies (data not shown), MUT31 has demonstrated 100% crop injury at rates of 75 g ai of imazamox per hectare and 100 g ai of imazapyr per hectare.

The double heterozygous A205V/MUT31 entries demonstrated significantly higher herbicide tolerance to both imazamox and imazapyr treatments versus the heterozygous A205V/-entries and versus the MUT31 entry on its own.

Based on this data, MUT31 when stacked with the A205V mutation in the heterozygous state provides stronger (enhanced) herbicide tolerance than the A205V mutation in the heterozygous state. Having a product that works in the heterozygous state at 2× the commercial product rate (100 g ai imazamox/ha and 160 g ai imazapyr/ha) is a great advantage to sunflower hybrid plant breeders over the current homozygous A205V/A205V product, saving both time and resources in the breeding of imadazolinone tolerant sunflowers.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. A seed of a sunflower plant of line MUT31, a representative sample of seed of said line having been deposited under ATCC Accession No. PTA-7839.

2. A sunflower plant, or a part thereof, produced by growing the seed of claim 1.

3. A tissue culture of regenerable cells produced from the plant, or part thereof, of claim 2.

4. A sunflower plant, or seed thereof, said sunflower plant regenerated from the tissue culture of claim 3, said plant having all the morphological and physiological trait of a sunflower plant of line MUT31, a representative sample of seed of said line having been deposited under ATCC Accession No. PTA-7839, wherein said seed thereof comprises the imidazolinone herbicide tolerance trait of line MUT31.

5. The sunflower plant of claim 4, wherein a transgene of interest was stably incorporated into its genome prior to regeneration.

6. A method for producing a hybrid sunflower seed, comprising crossing the plant of claim 2 with a different sunflower plant and harvesting the resultant hybrid sunflower seed.

7. A sunflower seed produced by the method of claim 6.

8. A sunflower plant grown from the seed of claim 7.

9. A method for producing a sunflower line comprising introducing a cytoplasmic male sterile trait or a restorer trait into the sunflower plant of line MUT31 of claim 2.

10. A MUT31 restorer sunflower line produced by the method of claim 9.

11. A MUT31 cytoplasmic male sterile sunflower line produced by the method of claim 9.

12. A method for producing a hybrid sunflower seed, comprising crossing the plant of claim 10 with a different sunflower plant and harvesting the resultant hybrid sunflower seed.

13. A method for producing a hybrid sunflower seed, comprising crossing the plant of claim 11 with a different sunflower plant and harvesting the resultant hybrid sunflower seed.

* * * * *